(12) United States Patent
DiMatteo et al.

(10) Patent No.: US 11,141,149 B2
(45) Date of Patent: Oct. 12, 2021

(54) METHODS AND DEVICES FOR REPAIRING AND ANCHORING DAMAGED TISSUE

(71) Applicant: DePuy Synthes Products, Inc., Raynham, MA (US)

(72) Inventors: Kristian DiMatteo, Waltham, MA (US); Gregory R. Whittaker, Stoneham, MA (US); Brooks J. Story, Franklin, MA (US); Mehmet Ziya Sengun, Canton, MA (US); Mark A. Capobianco, Westport, MA (US); Douglas Allen Fifolt, Wrentham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 120 days.

(21) Appl. No.: 15/991,189

(22) Filed: May 29, 2018

(65) Prior Publication Data

US 2018/0271523 A1  Sep. 27, 2018

Related U.S. Application Data

(63) Continuation of application No. 14/455,331, filed on Aug. 8, 2014, now Pat. No. 10,004,495, which is a (Continued)

(51) Int. Cl.
*A61B 17/06* (2006.01)
*A61B 17/04* (2006.01)
(Continued)

(52) U.S. Cl.
CPC .... *A61B 17/06166* (2013.01); *A61B 17/0401* (2013.01); *A61B 17/0469* (2013.01);
(Continued)

(58) Field of Classification Search
CPC .......... A61B 17/06166; A61B 17/0401; A61B 17/0469; A61B 2017/0409;
(Continued)

(56) References Cited

U.S. PATENT DOCUMENTS 233,475 A  10/1880  Cook et al.
261,501 A   7/1882  Wandermark
(Continued)

FOREIGN PATENT DOCUMENTS

CN  1891172 A  1/2007
CN  101056587 A  10/2007
(Continued)

OTHER PUBLICATIONS

Hoffmann et al., "Arthroscopic shoulder stablilization using Mitek anchors", Knee Surg., Sports Traumatol., Arthroscopy, Mar. 1995, vol. 3, Issue 1, 50-54.
(Continued)

*Primary Examiner* — Amy R Weisberg
(74) *Attorney, Agent, or Firm* — BakerHostetler

(57) ABSTRACT

Methods and devices are provided for anchoring suture to tissue, incorporating anchoring devices constructed substantially from suture. The anchoring devices are constructed as longitudinally extended, preformed knot configurations that upon deployment are reconfigured to form anchoring knots having an increased cross-section relative to the preformed knot configuration, for secure lodging in tissue. The anchoring devices are suitable for single and multi-anchor surgical procedures in soft tissue or bone, and multiple anchors can be delivered using a single delivery device.

20 Claims, 22 Drawing Sheets

Related U.S. Application Data continuation of application No. 12/509,112, filed on Jul. 24, 2009, now Pat. No. 8,828,053.

(51) Int. Cl.
A61B 17/00 (2006.01)
A61B 17/29 (2006.01)

(52) U.S. Cl.
CPC ............ *A61B 2017/00367* (2013.01); *A61B 2017/044* (2013.01); *A61B 2017/0409* (2013.01); *A61B 2017/0458* (2013.01); *A61B 2017/0464* (2013.01); *A61B 2017/0475* (2013.01); *A61B 2017/0477* (2013.01); *A61B 2017/0496* (2013.01); *A61B 2017/06052* (2013.01); *A61B 2017/2901* (2013.01)

(58) Field of Classification Search
CPC ...... A61B 2017/044; A61B 2017/0458; A61B 2017/00367; A61B 2017/0475; A61B 2017/0477; A61B 2017/0496; A61B 2017/06052; A61B 2017/2901; A61B 2017/0464
See application file for complete search history.

(56) References Cited

U.S. PATENT DOCUMENTS

| | | | |
|---|---|---|---|
| 330,087 A | 11/1885 | Binns |
| 400,743 A | 4/1889 | Brown |
| 2,490,364 A | 12/1949 | Livingston |
| 3,580,256 A | 5/1971 | Wilkinson et al. |
| 3,867,728 A | 2/1975 | Stubstad et al. |
| 3,908,677 A | 9/1975 | Beach |
| 3,987,806 A | 10/1976 | Gilbert |
| 4,006,747 A | 2/1977 | Kronenthal et al. |
| 4,235,238 A | 11/1980 | Ogiu et al. |
| 4,669,473 A | 6/1987 | Richards et al. |
| 4,741,330 A | 5/1988 | Hayhurst |
| 4,778,990 A | 10/1988 | Laughlin |
| 4,788,990 A | 12/1988 | Wisegerber |
| 4,994,028 A | 2/1991 | Leonard et al. |
| 4,994,069 A | 2/1991 | Ritchart et al. |
| 5,021,059 A | 6/1991 | Kensey et al. |
| 5,041,129 A | 8/1991 | Hayhurst et al. |
| 5,053,046 A | 10/1991 | Janese |
| 5,062,344 A | 11/1991 | Gerker |
| 5,120,596 A | 6/1992 | Yamada |
| 5,129,912 A | 7/1992 | Noda et al. |
| 5,156,616 A | 10/1992 | Meadows et al. |
| 5,269,809 A | 12/1993 | Hayhurst et al. |
| 5,281,238 A | 1/1994 | Chin et al. |
| 5,403,348 A | 4/1995 | Bonutti |
| 5,417,691 A | 5/1995 | Hayhurst |
| 5,464,426 A | 11/1995 | Bonutti |
| 5,478,353 A | 12/1995 | Yoon |
| 5,507,754 A | 4/1996 | Green et al. |
| 5,522,846 A | 6/1996 | Bonutti |
| 5,527,343 A | 6/1996 | Bonutti |
| 5,540,703 A | 7/1996 | Barker et al. |
| 5,549,630 A | 8/1996 | Bonutti |
| 5,562,684 A | 10/1996 | Kammerer |
| 5,562,736 A | 10/1996 | Ray et al. |
| 5,571,189 A | 11/1996 | Kuslich |
| 5,584,862 A | 12/1996 | Bonutti |
| 5,601,557 A | 2/1997 | Hayhurst |
| 5,626,614 A | 5/1997 | Hart |
| 5,628,756 A | 5/1997 | Barker et al. |
| 5,643,319 A | 7/1997 | Green et al. |
| 5,649,945 A | 7/1997 | Ray et al. |
| 5,699,657 A | 12/1997 | Paulson |
| 5,702,462 A | 12/1997 | Oberlander |
| 5,728,109 A | 3/1998 | Schulze et al. |
| 5,733,306 A | 3/1998 | Bonutti |
| 5,824,093 A | 10/1998 | Ray et al. |
| 5,906,626 A | 5/1999 | Carrillo |
| 5,941,900 A | 8/1999 | Bonutti |
| 5,944,739 A | 8/1999 | Zlock et al. |
| 5,948,002 A | 9/1999 | Bonutti |
| 5,951,590 A | 9/1999 | Goldfarb |
| 5,957,953 A | 9/1999 | Dipoto et al. |
| 5,970,697 A | 10/1999 | Jacobs et al. |
| 5,989,252 A | 11/1999 | Fumex |
| 6,056,773 A | 5/2000 | Bonutti |
| 6,068,648 A | 5/2000 | Cole et al. |
| 6,077,292 A | 6/2000 | Bonutti |
| 6,110,183 A | 8/2000 | Cope |
| 6,113,611 A | 9/2000 | Allen et al. |
| 6,146,422 A | 11/2000 | Lawson |
| 6,179,860 B1 | 1/2001 | Fulton et al. |
| 6,187,048 B1 | 2/2001 | Milner et al. |
| 6,209,550 B1 | 4/2001 | Powell, Jr. |
| 6,224,630 B1 | 5/2001 | Bao et al. |
| 6,245,107 B1 | 6/2001 | Ferree |
| 6,287,325 B1 | 9/2001 | Bonutti |
| 6,296,659 B1 | 10/2001 | Foerster |
| 6,306,159 B1 | 10/2001 | Schwartz et al. |
| 6,325,816 B1 | 12/2001 | Fulton et al. |
| 6,409,742 B1 | 6/2002 | Fulton et al. |
| 6,432,123 B2 | 8/2002 | Schwartz et al. |
| 6,482,235 B1 | 11/2002 | Lambrecht et al. |
| 6,508,839 B1 | 1/2003 | Lambrecht et al. |
| 6,511,498 B1 | 1/2003 | Fumex |
| 6,530,933 B1 | 3/2003 | Yeung et al. |
| 6,579,291 B1 | 6/2003 | Keith et al. |
| 6,592,625 B2 | 7/2003 | Cauthen |
| 6,638,291 B1 | 10/2003 | Ferrera et al. |
| 6,656,182 B1 | 12/2003 | Hayhurst |
| 6,689,125 B1 | 2/2004 | Keith et al. |
| 6,719,797 B1 | 4/2004 | Ferree |
| 6,758,855 B2 | 7/2004 | Fulton et al. |
| 6,964,674 B1 | 11/2005 | Matsuura et al. |
| 6,972,027 B2 | 12/2005 | Fallin et al. |
| 6,984,247 B2 | 1/2006 | Cauthen |
| 6,986,775 B2 | 1/2006 | Morales et al. |
| 6,991,643 B2 | 1/2006 | Saadat |
| 6,997,956 B2 | 2/2006 | Cauthen |
| 7,004,970 B2 | 2/2006 | Cauthen et al. |
| 7,033,393 B2 | 4/2006 | Gainor et al. |
| 7,033,395 B2 | 4/2006 | Cauthen |
| 7,041,052 B2 | 5/2006 | Saadat et al. |
| 7,048,754 B2 | 5/2006 | Martin et al. |
| 7,052,516 B2 | 5/2006 | Cauthen et al. |
| 7,128,708 B2 | 10/2006 | Saadat et al. |
| 7,153,312 B1 | 12/2006 | Torrie et al. |
| 7,189,235 B2 | 3/2007 | Cauthen |
| 7,285,124 B2 | 10/2007 | Foerster |
| 7,303,575 B2 | 12/2007 | Ogle |
| 7,326,221 B2 | 2/2008 | Sakamoto et al. |
| 7,329,279 B2 | 2/2008 | Haug et al. |
| 7,335,221 B2 | 2/2008 | Collier et al. |
| 7,347,863 B2 | 3/2008 | Rothe et al. |
| 7,390,332 B2 | 6/2008 | Selvitelli et al. |
| 7,468,074 B2 | 12/2008 | Caborn et al. |
| 7,491,212 B2 | 2/2009 | Sikora et al. |
| 7,494,496 B2 | 2/2009 | Swain et al. |
| 7,601,165 B2 | 10/2009 | Stone |
| 7,615,076 B2 | 11/2009 | Cauthen et al. |
| 7,621,925 B2 | 11/2009 | Saadat et al. |
| 7,651,509 B2 | 1/2010 | Bojarski et al. |
| 7,658,750 B2 | 2/2010 | Li |
| 7,666,193 B2 | 2/2010 | Starksen et al. |
| 7,670,379 B2 | 3/2010 | Cauthen |
| 7,670,380 B2 | 3/2010 | Cauthen, III |
| 7,678,135 B2 | 3/2010 | Maahs et al. |
| 7,731,732 B2 | 6/2010 | Ken |
| 7,736,379 B2 | 6/2010 | Ewers et al. |
| 7,749,250 B2 | 7/2010 | Stone et al. |
| 7,749,273 B2 | 7/2010 | Cauthen et al. |
| 7,753,941 B2 | 7/2010 | Keith et al. |
| 7,776,096 B2 | 8/2010 | Cauthen |
| 7,828,850 B2 | 11/2010 | Cauthen et al. |
| 7,846,208 B2 | 12/2010 | Cauthen et al. |

(56) References Cited

U.S. PATENT DOCUMENTS

| | | |
|---|---|---|
| 7,857,830 B2 | 12/2010 | Stone et al. |
| 7,905,904 B2 | 3/2011 | Stone et al. |
| 7,905,923 B2 | 3/2011 | Keith et al. |
| 7,909,851 B2 | 3/2011 | Stone et al. |
| 7,909,879 B2 | 3/2011 | Cauthen |
| 7,922,768 B2 | 4/2011 | Cauthen et al. |
| 7,935,147 B2 | 5/2011 | Wales |
| 7,951,201 B2 | 5/2011 | Cauthen et al. |
| 7,959,650 B2 | 6/2011 | Kaiser et al. |
| 7,963,992 B2 | 6/2011 | Cauthen et al. |
| 7,985,257 B2 | 7/2011 | Cauthen et al. |
| 7,993,405 B2 | 8/2011 | Cauthen et al. |
| 7,998,108 B2 | 8/2011 | Nazzaro et al. |
| 8,034,112 B2 | 10/2011 | Cauthen et al. |
| 8,048,160 B2 | 11/2011 | Cauthen |
| 8,083,768 B2 | 12/2011 | Ginn et al. |
| 8,088,130 B2 | 1/2012 | Kaiser et al. |
| 8,088,165 B2 | 1/2012 | Cauthen et al. |
| 8,100,914 B2 | 1/2012 | Cauthen et al. |
| 8,118,836 B2 | 2/2012 | Denham et al. |
| 8,128,640 B2 | 3/2012 | Harris et al. |
| 8,128,658 B2 | 3/2012 | Kaiser et al. |
| 8,128,698 B2 | 3/2012 | Bentley et al. |
| 8,137,382 B2 | 3/2012 | Denham et al. |
| 8,216,253 B2 | 7/2012 | Saadat et al. |
| 8,216,260 B2 | 7/2012 | Lam et al. |
| 8,298,291 B2 | 10/2012 | Ewers et al. |
| 8,696,716 B2 | 4/2014 | Kartalian et al. |
| 8,814,903 B2 | 8/2014 | Sengun et al. |
| 8,828,053 B2 | 9/2014 | Sengun et al. |
| 8,920,436 B2 | 12/2014 | Lam et al. |
| 8,926,634 B2 | 1/2015 | Rothe et al. |
| 9,023,081 B2 | 5/2015 | Maiorino et al. |
| 9,149,266 B2 | 10/2015 | Lamson et al. |
| 9,173,645 B2 | 11/2015 | Overes et al. |
| 2002/0029782 A1 | 3/2002 | Linderoth |
| 2002/0065536 A1 | 5/2002 | Hart et al. |
| 2002/0115999 A1 | 8/2002 | McDevitt et al. |
| 2002/0143359 A1 | 10/2002 | Fulton et al. |
| 2002/0188301 A1 | 12/2002 | Dallara et al. |
| 2003/0060835 A1 | 3/2003 | Wenstrom |
| 2003/0167071 A1 | 9/2003 | Martin et al. |
| 2004/0097980 A1 | 5/2004 | Ferree |
| 2004/0122473 A1 | 6/2004 | Ewers et al. |
| 2004/0153074 A1 | 8/2004 | Bojarski et al. |
| 2004/0153704 A1 | 8/2004 | Bragulla et al. |
| 2004/0162618 A1 | 8/2004 | Mujwid et al. |
| 2004/0225183 A1 | 11/2004 | Michlitsch et al. |
| 2004/0225359 A1 | 11/2004 | Bojarski et al. |
| 2004/0243171 A1 | 12/2004 | Fulton et al. |
| 2004/0267257 A1 | 12/2004 | Bourne et al. |
| 2005/0080422 A1 | 4/2005 | Otte et al. |
| 2005/0228406 A1 | 10/2005 | Bose |
| 2005/0228448 A1 | 10/2005 | Li |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0256582 A1 | 11/2005 | Ferree |
| 2005/0277966 A1 | 12/2005 | Ewers et al. |
| 2005/0277981 A1 | 12/2005 | Maahs et al. |
| 2005/0283192 A1 | 12/2005 | Torrie et al. |
| 2005/0283246 A1 | 12/2005 | Cauthen et al. |
| 2006/0064126 A1 | 3/2006 | Fallin et al. |
| 2006/0178680 A1 | 8/2006 | Nelson et al. |
| 2006/0190042 A1 | 8/2006 | Stone et al. |
| 2006/0206119 A1 | 9/2006 | Chu |
| 2006/0224166 A1 | 10/2006 | Weisenburgh et al. |
| 2006/0259076 A1 | 11/2006 | Burkhart et al. |
| 2006/0265008 A1 | 11/2006 | Maruyama et al. |
| 2006/0271073 A1 | 11/2006 | Lam et al. |
| 2006/0271074 A1 | 11/2006 | Ewers et al. |
| 2007/0010857 A1 | 1/2007 | Sugimoto et al. |
| 2007/0027476 A1 | 2/2007 | Harris et al. |
| 2007/0073320 A1 | 3/2007 | Mikkaichi et al. |
| 2007/0083236 A1 | 4/2007 | Sikora et al. |
| 2007/0100348 A1 | 5/2007 | Cauthen et al. |
| 2007/0129804 A1 | 6/2007 | Bentley et al. |
| 2007/0142846 A1 | 6/2007 | Catanese et al. |
| 2007/0156245 A1 | 7/2007 | Cauthen et al. |
| 2007/0162054 A1 | 7/2007 | Horaguchi |
| 2007/0162120 A1 | 7/2007 | Bouffier |
| 2007/0185532 A1* | 8/2007 | Stone ............... A61B 17/0469 606/232 |
| 2007/0255285 A1 | 11/2007 | Trieu |
| 2007/0276433 A1 | 11/2007 | Huss |
| 2008/0009888 A1 | 1/2008 | Ewers et al. |
| 2008/0015635 A1 | 1/2008 | Olsen et al. |
| 2008/0015636 A1 | 1/2008 | Olsen et al. |
| 2008/0033487 A1 | 2/2008 | Schwartz et al. |
| 2008/0039873 A1 | 2/2008 | Bonutti et al. |
| 2008/0086155 A1 | 4/2008 | Rothe et al. |
| 2008/0097484 A1 | 4/2008 | Lim et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shurnas |
| 2008/0177304 A1 | 7/2008 | Westra et al. |
| 2008/0188893 A1 | 8/2008 | Selvitelli et al. |
| 2008/0195145 A1 | 8/2008 | Bonutti et al. |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0243151 A1 | 10/2008 | Binmoeller et al. |
| 2008/0269781 A1 | 10/2008 | Funamura et al. |
| 2008/0281355 A1 | 11/2008 | Mayer et al. |
| 2008/0294193 A1 | 11/2008 | Schwartz et al. |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0030522 A1 | 1/2009 | Cauthen et al. |
| 2009/0036937 A1 | 2/2009 | Cauthen et al. |
| 2009/0036989 A1 | 2/2009 | Cauthen et al. |
| 2009/0036990 A1 | 2/2009 | Cauthen et al. |
| 2009/0062846 A1 | 3/2009 | Ken |
| 2009/0062847 A1 | 3/2009 | Ken |
| 2009/0062848 A1 | 3/2009 | Ken |
| 2009/0062850 A1 | 3/2009 | Ken |
| 2009/0062854 A1 | 3/2009 | Kaiser et al. |
| 2009/0069823 A1 | 3/2009 | Foerster et al. |
| 2009/0076547 A1 | 3/2009 | Sugimoto et al. |
| 2009/0082805 A1 | 3/2009 | Kaiser et al. |
| 2009/0157184 A1 | 6/2009 | Cauthen et al. |
| 2009/0228042 A1 | 9/2009 | Koogle et al. |
| 2009/0259260 A1 | 10/2009 | Bentley et al. |
| 2009/0306711 A1 | 12/2009 | Stone et al. |
| 2010/0049212 A1 | 2/2010 | Caborn et al. |
| 2010/0069923 A1 | 3/2010 | Nguyen et al. |
| 2010/0094337 A1* | 4/2010 | Maiorino ............ A61B 17/0485 606/228 |
| 2010/0094425 A1 | 4/2010 | Bentley et al. |
| 2010/0121376 A1 | 5/2010 | Li |
| 2010/0292731 A1 | 11/2010 | Gittings et al. |
| 2011/0022083 A1 | 1/2011 | Dimatteo et al. |
| 2011/0022084 A1 | 1/2011 | Sengun et al. |
| 2011/0077667 A1 | 3/2011 | Singhatat et al. |
| 2011/0082472 A1 | 4/2011 | Harris et al. |
| 2011/0106151 A1 | 5/2011 | McDevitt et al. |
| 2011/0172701 A1 | 7/2011 | Wales et al. |
| 2011/0270278 A1 | 11/2011 | Overes et al. |
| 2012/0004669 A1 | 1/2012 | Overes et al. |

(56) References Cited

U.S. PATENT DOCUMENTS

| | | | |
|---|---|---|---|
| 2012/0013422 | A1 | 1/2012 | Tenno et al. |
| 2012/0035654 | A1 | 2/2012 | Belson |
| 2012/0046693 | A1 | 2/2012 | Denham et al. |
| 2012/0053630 | A1 | 3/2012 | Denham et al. |
| 2012/0109156 | A1 | 5/2012 | Overes et al. |
| 2012/0130422 | A1 | 5/2012 | Hootstein |
| 2012/0143215 | A1 | 6/2012 | Corrao et al. |
| 2012/0150223 | A1 | 6/2012 | Manos et al. |
| 2012/0197271 | A1 | 8/2012 | Astorino et al. |
| 2012/0215257 | A1 | 8/2012 | McDevitt et al. |
| 2013/0110165 | A1 | 5/2013 | Burkhart et al. |
| 2014/0074157 | A1 | 3/2014 | Hirotsuka et al. |
| 2014/0243859 | A1 | 8/2014 | Robinson |
| 2014/0336703 | A1 | 11/2014 | Sengun et al. |
| 2015/0038992 | A1 | 2/2015 | Dimatteo et al. |
| 2015/0173740 | A1 | 6/2015 | Sugimoto et al. |

FOREIGN PATENT DOCUMENTS

| | | |
|---|---|---|
| DE | 4207854 A1 | 9/1993 |
| EP | 0834281 A1 | 4/1998 |
| EP | 0838197 A2 | 4/1998 |
| EP | 1741400 | 1/2007 |
| EP | 1804683 A2 | 7/2007 |
| EP | 1938760 A1 | 7/2008 |
| EP | 1964520 A2 | 9/2008 |
| EP | 2238944 A2 | 10/2010 |
| EP | 2663240 A1 | 11/2013 |
| EP | 2663242 A1 | 11/2013 |
| JP | 2006-516468 A | 7/2006 |
| JP | 2007-536007 A | 12/2007 |
| JP | 2009-500105 A | 1/2009 |
| JP | 2010-165577 A | 7/2010 |
| JP | 2011-025035 | 2/2011 |
| JP | 2013-525023 | 6/2013 |
| WO | 92/11810 A1 | 7/1992 |
| WO | 99/22648 A1 | 5/1999 |
| WO | 03/96910 | 11/2003 |
| WO | 2004/071307 A2 | 8/2004 |
| WO | 2005/011463 A2 | 2/2005 |
| WO | 2005/065553 A1 | 7/2005 |
| WO | 2006/037639 A1 | 4/2006 |
| WO | 2006/039296 A2 | 4/2006 |
| WO | 2006/117398 A2 | 11/2006 |
| WO | 2007/005394 A1 | 1/2007 |
| WO | 2007/037326 A1 | 4/2007 |
| WO | 2008/010738 A2 | 1/2008 |
| WO | 2008/048667 A1 | 4/2008 |
| WO | 2009/126781 A1 | 10/2009 |
| WO | 2009/146402 A1 | 12/2009 |
| WO | 2010/088561 A2 | 8/2010 |
| WO | 2011/137159 A1 | 11/2011 |
| WO | 2012/006161 A2 | 1/2012 |
| WO | 2012/096706 | 7/2012 |
| WO | 2012/096707 A1 | 7/2012 |

OTHER PUBLICATIONS

Hampton et al., "Healing Potential of the Anulus Fibrosus," Spine, Apr. 1989, 14(4), 398-401.
European Search Report for Application No. 10251328.0 dated Oct. 29, 2010.
European Patent Application No. 05802651.9: European Search Report, dated Aug. 31, 2009, 7 pages.
Elongated Suturing Element and Method of Using the Same, U.S. Appl. No. 61/328,251.
Edgerton et al., "Augmentation Mammaplasty: Psychiatric Implications and Surgical Indications," Plastic & Reconstructive Surgery, Apr. 1958, 21(4), 279-305.
Dodge, Jr. et al., "Use of Polyvinyl Sponge in Neurosurgery," Journal of Neurosurgery, May 1954, 11(3), 258-261.
Devices and Methods of Intervertebral Disc Augmentation, U.S. Appl. No. 60/149,490.
Devices and methods for the treatment of spinal disorders, U.S. Appl. No. 60/263,343.
Coen et al., "An anatomic evaluation of T-Fix suture device placement for arthroscopic all-inside meniscal repair," Arthroscopy: The Journal of Arthroscopic and Related Surgery, Apr. 1999, 15(3), 275-280.
Cobey, M., "Arthroplasties using compressed ivalon sponge ("intramedic sponge") long-term follow-up studies in 109 cases," Clinical Orthopaedics and Related Research, Sep.-Oct. 1967, 54, 139-144.
Clifford Ashley "The Ashley Book of Knots" 1944.
Cayenne Medical, Crossfix Meniscal Repair System, Surgical Technique Guide, Jul. 2009, 4 pages.
Cauthen,"Microsurgical Annular Reconstruction (Annuloplasty) Following Lumbar Microdiscectomy: Preliminary Report of a New Technique", CNS Boston Massachusetts, Spine & Peripheral Nerves Section (abstract only), http://abstracts.neurosurgeon.org/view.php?id=2790, accessed Oct. 6, 2010, 1999, 1 page.
Cauthen, J., "Microsurgical Annular Reconstruction (Annuloplasty) Following Lumbar Microdiscectomy: A New Technique," Draft Abstract, Sep. 4, 1998, 4 pages.
Cauthen, J., "Microsurgical Annular Reconstruction (Annuloplasty) Following Lumbar Microdiscectomy: A New Technique," Abstract, AANS CNS Section on Disorders of the Spine and Peripheral Nerves Annual Meeting, 1999, 2 pages.
Cauthen, J., "Annulotomy Study Table", Feb. 8, 1999, 1 page.
Caborn, D., "Meniscal Repair with the Fast T-Fix Suture System," Smith & Nephew Technique Plus Illustrated Guide, Mar. 2002, 10 pages.
Burg et al., "Modulation of Surface and Bulk Properties of Biomedical Polymers," Annals of the New York Academy of Sciences, Dec. 1997, 831, 217-222.
Brinckmann et al., "A laboratory model of lumbar disc protrusion", Fissure and Fragment Institut fur Experimentelle Biomechanik, Universitat, Munster, German, Spine (Phila., PA 1976) Jan. 15, 1994,19(2): 228-235.
Biomet Maxfire Technique Guide, Meniscal Repair, 1994, 16 pages.
Barrett et al., "T-Fix endoscopic meniscal repair: technique and approach to different types of tears," Arthroscopy: The Journal of Arthroscopic and Related Surgery, Apr. 1995, 11(2), 245-251.
Ashley, "The Ashley Book of Knots", 1993.
Arthrex, Inc., "Arthroscopic Meniscal Repair using the Meniscal Cinch: Surgical Technique," www.arthrex.com, copyrights 2008, 6 pages.
Annulotomy Closure Device, U.S. Appl. No. 60/154,969.
Anchor Body, U.S. Appl. No. 61/443,142.
Ahlgren et al., "Effect of anular repair on the healing strength of the intervertebral disc: a sheep model," Spine, Sep. 1, 2000, 25(17), 2165-2170.
Ahlgren et al., "Anular incision technique on the strength and multidirectional flexibility of the healing intervertebral disc," Spine, Apr. 15, 1994, 19(8), 948-954.
Abstracts of the 7th Annual Meeting of the Japanese Society of Microsurgery, Oct. 1980, Niigata, Japan, 8 pages.
Yasargil, M. G., "Microsurgical Operation of Herniated Lumbar Disc," Advances in Neurosurgery, Lumbar Disc Adult Hydrocephalus, Springer-Verlag, 1977, 4(81), p. 81.
Wound Closure Devices and Methods, U.S. Appl. No. 09/453,120.
Wageck et al., "Arthroscopic meniscal suture with the "double-loop technique"," Arthroscopy: The Journal of Arthroscopic and Related Surgery, Feb. 1997, 13(1), 120-123.
Vuono-Hawkins et al., "Mechanical Evaluation of a Canine Intervertebral Disc Spacer: In Situ and In Vivo Studies", Journal of Orthopaedic Research, Jan. 1994, 119-127.
Urbaniak et al., "Replacement of intervertebral discs in chimpanzees by silicone-dacron implants: a preliminary report," J. Biomed. Mater. Res. Symposium, May 1973, 7(4), 165-186.
Unipoint Industries, Inc., "Polyvinyl Alcohol Foam for Surgical and Industrial Use: Data Sheets," Jul. 15, 1989, 6 pages.
U.S. Appl. No. 13/095,192: Restriction Requirement, dated Sep. 6, 2012, 10 pages.
U.S. Appl. No. 12/509,112: Restriction Requirement, dated Nov. 17, 2011, 8 pages.

(56) References Cited

OTHER PUBLICATIONS

U.S. Appl. No. 12/509,112: Restriction Requirement, dated Apr. 10, 2012, 6 pages.
U.S. Appl. No. 12/509,112: Non-Final Office Action, dated Jul. 12, 2012, 8 pages.
The Free Dictionary, definition of "knot", http://medical-dictionary.H1efreedisctionary.corn/knot as accessed on Jun. 21, 2016, 5 pages.
Spinal Disc Annulus Reconstruction Method and Spinal Disc Annulus Stent, U.S. Appl. No. 60/160,710.
Spinal Disc Annulus Reconstruction Method and Spinal Disc Annulus Stent, U.S. Appl. No. 09/484,706.
Spinal Disc and Nucleus Repair/Augmentation Methods and Apparatus, U.S. Appl. No. 60/148,913.
Southwick et al., "Prosthetic Replacement of Chest-Wall Defects: An Experimental and Clinical Study", A. M.A. Archives of Surgery, 1956, 72, 901-907.
Snyder, S.J., "Shoulder Arthroscopy: Arthroscopic Treatment of the Acromioclavicular Joint", Chapter 13, 2nd Edition, 2003, 167-183.
Smith & Nephew Endoscopy, "Fast-Fix Meniscal Repair System: Technique Information," http://endo.smith-nephew.com/no/node.aspNodeId=3045, Accessed Apr. 26, 2011, 3 pages.
Smith & Nephew Endoscopy, "Endoscopic Meniscal Repair Using the T-Fix TM" Smith & Nephew, May 1996, 16 pages.
Silver et al., "Cartilage Wound Healing: An Overview," Otolaryngol. Clin. North Am., Oct. 1995, 28(5), 847-863.
Sgaglione et al., "All-Inside Meniscal Repair with the Ultra Fast-Fix TM Meniscal Repair System," Smith & Nephew Knee Series Technique Guide, Feb. 2008, 12 pages.
Sgaglione et al., "All-Inside Meniscal Repair with the Ultra Fast-Fix TM Meniscal Repair System," Smith & Hephew Knee Series Technique Guide, Feb. 2008,12 pages.
Ray, C. D., "Prosthetic Disc Nucleus Implants: Update," North American Spine Society 13th Annual Meeting, 1999, 252-253.
PR Newswire, "Smith & Nephew Launches Fast-Fix TM AB Meniscal Repair System," http://www.pmewswire.com/news-releases/smith-nephew-launches-fast-fixtm-ab-menis . . . , Accessed Aug. 23, 2010, 1 page.
Peters et al., "Ivalon Breast Prostheses: Evaluation 19 Years after Implantation," Plastic and Reconstructive Surgery, Apr. 1981, 67(4), 514-518.
Panjabi et al., "Intrinsic Disc Pressure as a Measure of Integrity of the Lumbar Spine," Spine, Aug. 1988, 13(8), 913-917.
Osti et al., "Annular Tears and Disc Degeneration in the Lumbar Spine. A post-mortem study of 135 discs," The Journal of Bone and Joint Surgery, Sep. 1992, 74(5), 678-682.
Osti et al., "1990 Volvo Award in Experimental Studies: Anulus Tears and Intervertebral Disc Degeneration: An Experimental Study Using an Animal Model," Spine, Aug. 1990, 15(8), 762-767.
Ordway et al., "Failure Properties of a Hydrogel Nucleus in the Intervertebral Disc," North American Spine Society, Oct. 22-25, 1997, 168-169.
Multi-tire knot anchor deployment system, U.S. Appl. No. 61/461,490.
Multi-Fire Knot Anchor Deployment System, U.S. Appl. No. 61/432,755.
Mitek Brochure, Rapid Loe, "Surgical Technique Guide for Repair of Meniscal Tears", 2001, 6 pages.
Methods and Devices for Intervertebral Disc Repair, U.S. Appl. No. 60/161,085.
Meniscal Repair Device, U.S. Appl. No. 60/113,548.
Mayer et al., "Percutaneous Endoscopic Lumbar Discectomy (PELO)", Neurosurg., Rev., Jun. 1993, 115-120.
Mayer et al., "Endoscopic Discectomy in Pediatric and Juvenile Lumbar Disc Herniation's", Journal of the Pediatric Orthopaedics, Part B, Jan. 1996, 39-43.
Maroon et al., "Microdiscectomy versus Chemonucleolysis", Neurosurgery, vol. 16(5), 644-649, May 1985.
Malemud, C. J., "The Role of Growth Factors in Cartilage Metabolism," Rheum. Dis. Clin. North Am., Aug. 1993, 19(3), 569-580.
Liu et al., "Morphologic Characterization of Polyvinyl Sponge (Ivalon) Breast Prosthesis," Archives of Pathol. & Lab. Medicine, Sep. 1996, 120(9), 876-878.
Lehmann et al., "Refinements in technique for open lumbar discectomy," International Society for the Study of the Lumbar Spine, 1997, 2 pages.
Kusaka et al., "The Effect of Annulus Fibrosus Perforation on the Intradiscal Matrix Strain of the Axially Loaded Intervertebral Disc," Transactions of the 44th Annual Meeting, Orthopaedic Research Society, Mar. 16-19, 1998, New Orleans, Louisiana, 23(1), p. 190-32 (Abstract).
Kroschwitz, J. I., "Concise Encyclopedia of Polymer Science and Engineering: Vinyl Alcohol Polymers," Wiley & Sons, 1990, 1233-1236.
Kotilainen et al., "Microsurgical treatment of lumbar disc herniation: Follow-up of 237 patients," Acta Neurochirurgica, 1993, 120(3-4) 143-149.
Knot anchor implant, U.S. Appl. No. 61/398,699.
Klinger, "Proceedings of the 1976 Meeting of the Deutsche Gesellschaft for Neurochirurgica in Berlin", Acta Neurochirurgica, Sep. 1977, vol. 36, Issue 3-4, 265-294.
Kambin et al., "Development of degenerative spondylosis of the lumbar spine after partial discectomy. Comparison of laminotomy, discectomy, and posterolateral discectomy," Spine, Mar. 1, 1995, 20(5), 599-607.
International Patent Application No. PCT/US2011/058071: International Search Report and Written Opinion dated Feb. 6, 2012, 14 pages.
International Patent Application No. PCT/US2011/058065: International Search Report and Written Opinion dated Apr. 5, 2012, 23 pages.
International Patent Application No. PCT/US2011/042384: International Search Report and Written Opinion dated Feb. 6, 2012, 26 pages.
International Patent Application No. PCT/US2011/034084: International Search Report and Written Opinion dated Jul 1, 2011, 5 pages.
International Patent Application No. PCT/US05/34495: International Search Report dated Apr. 4, 2007, 2 pages.

* cited by examiner

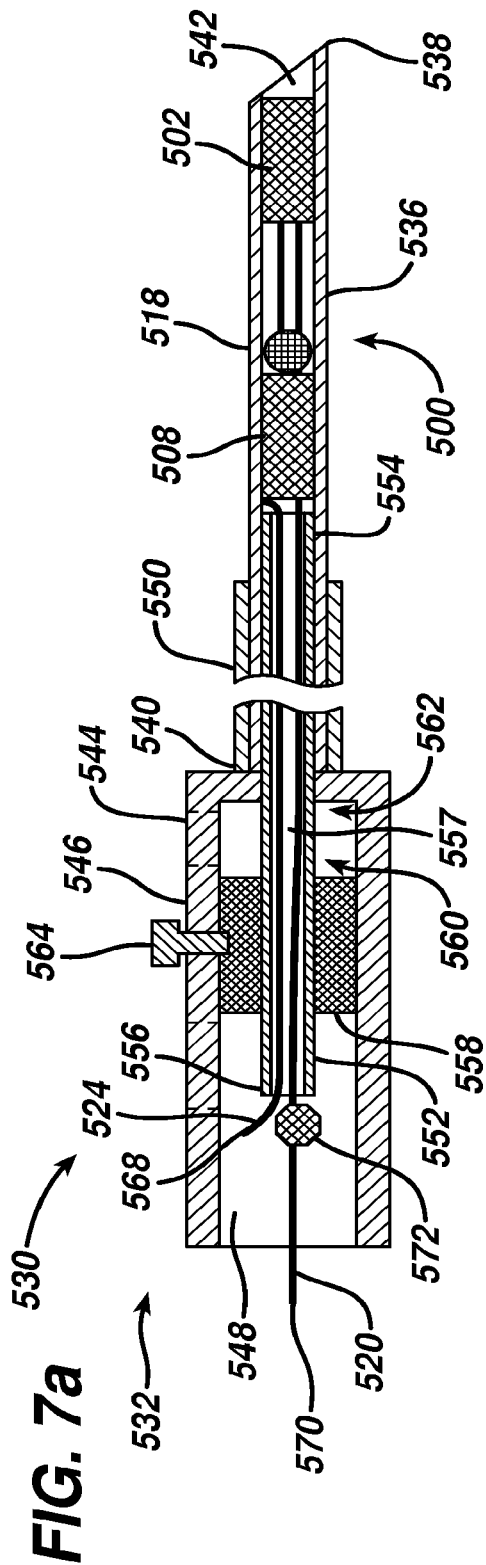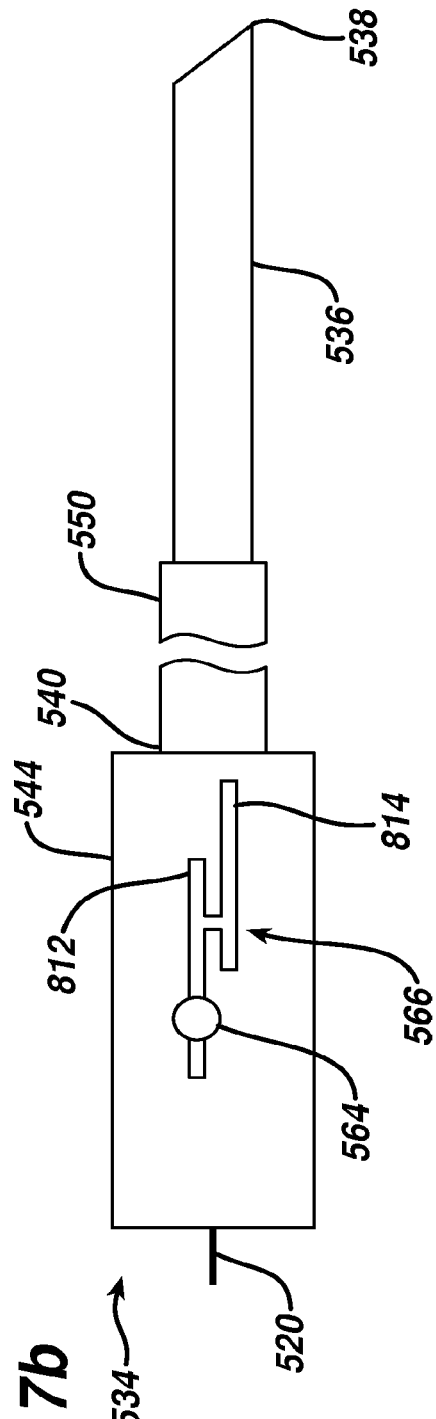

FIG. 8a
FIG. 8b
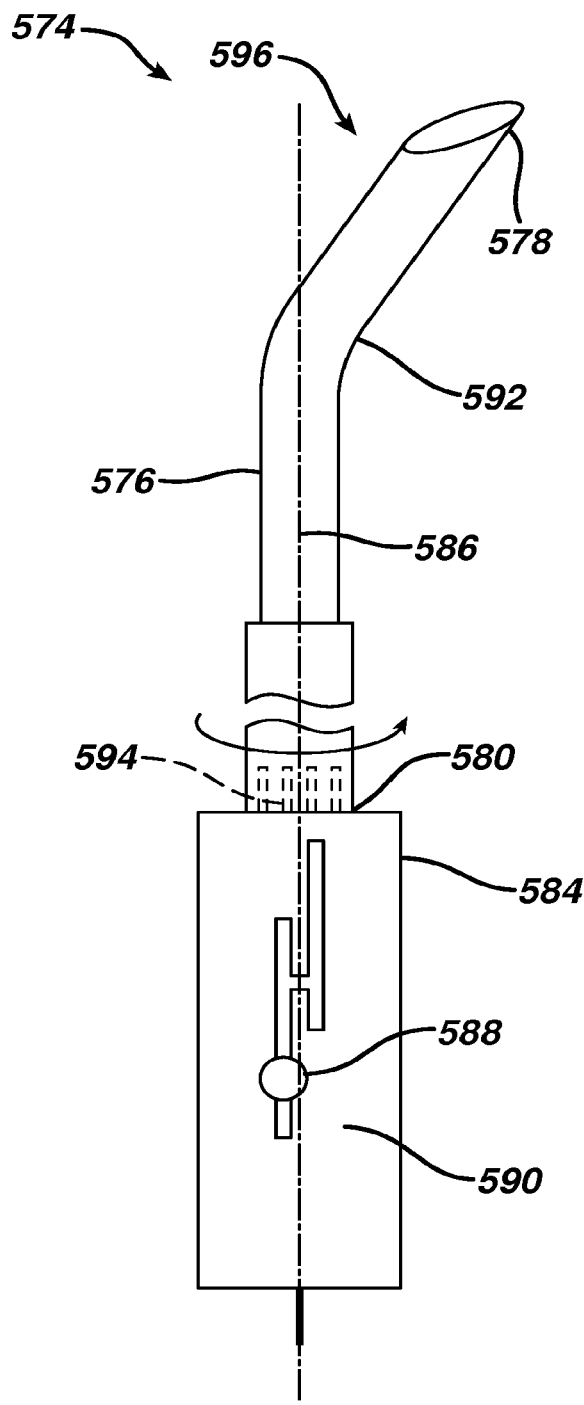
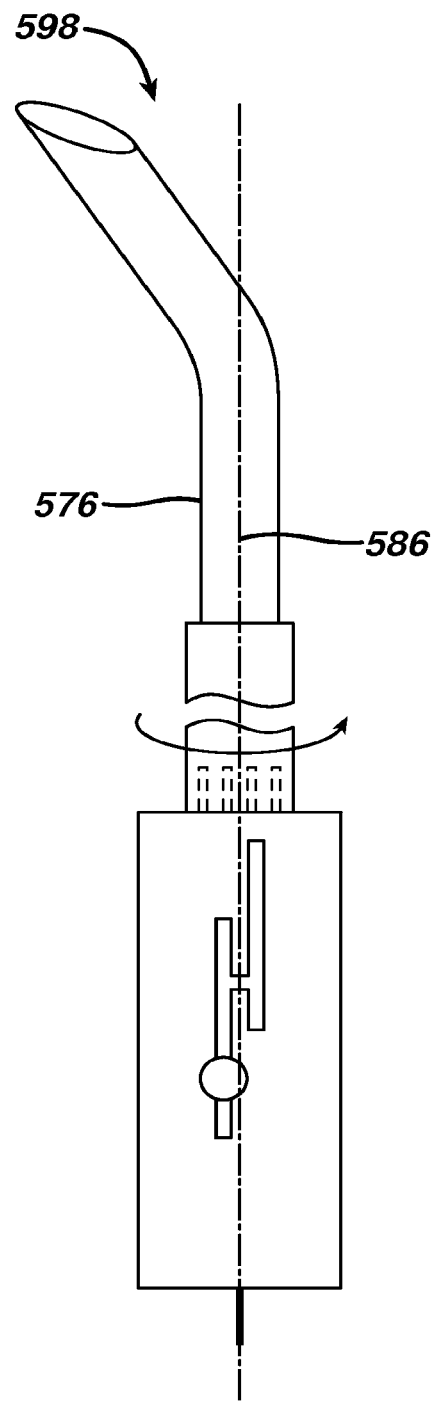

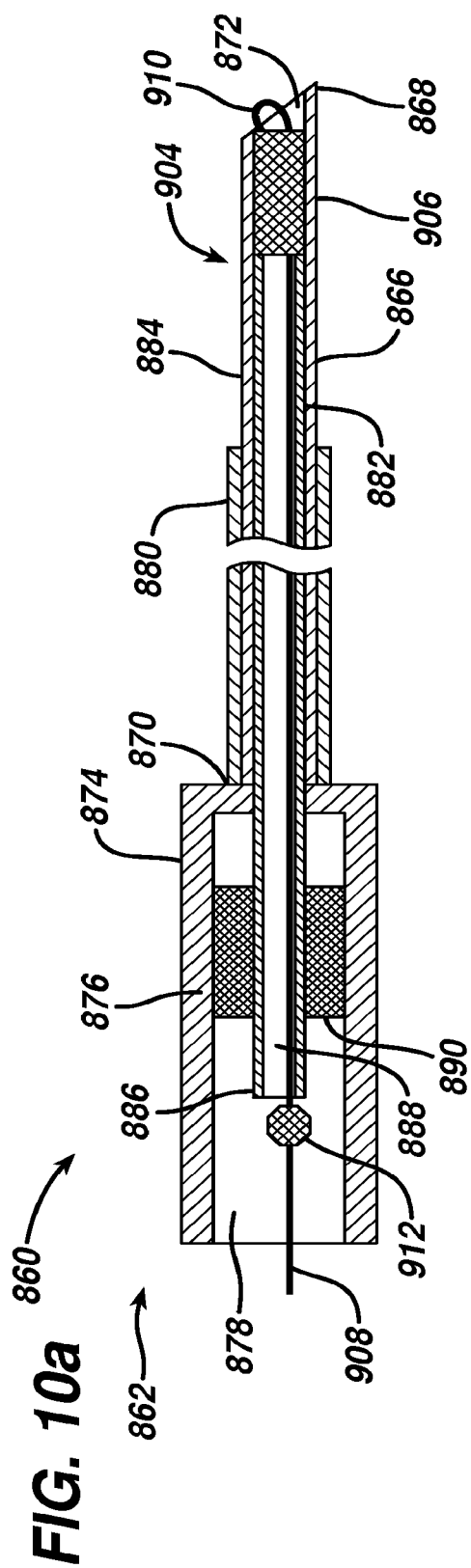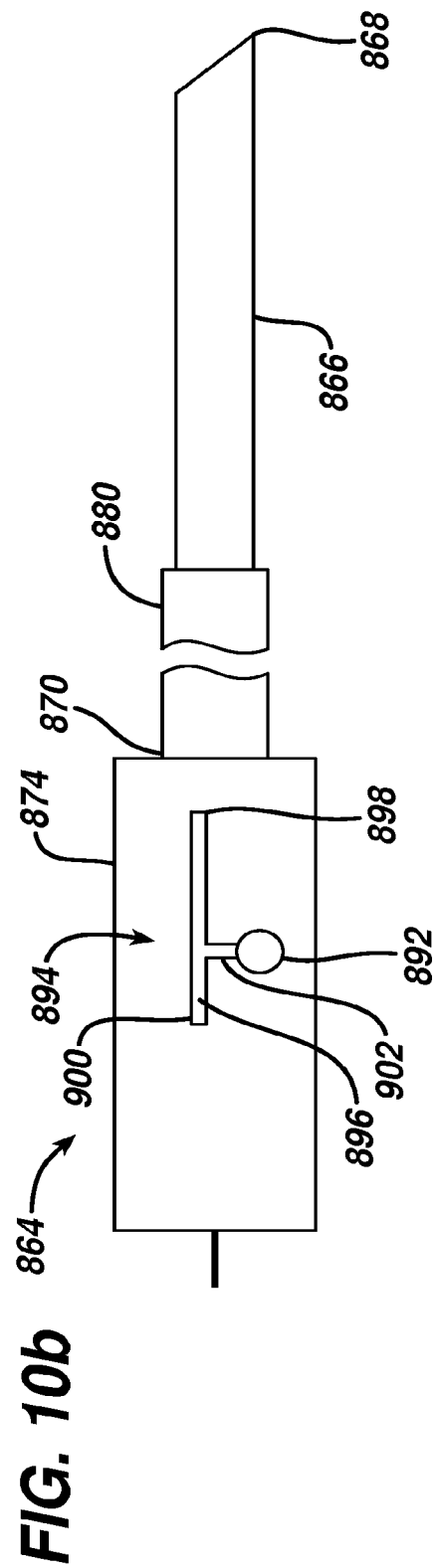
FIG. 10a
FIG. 10b

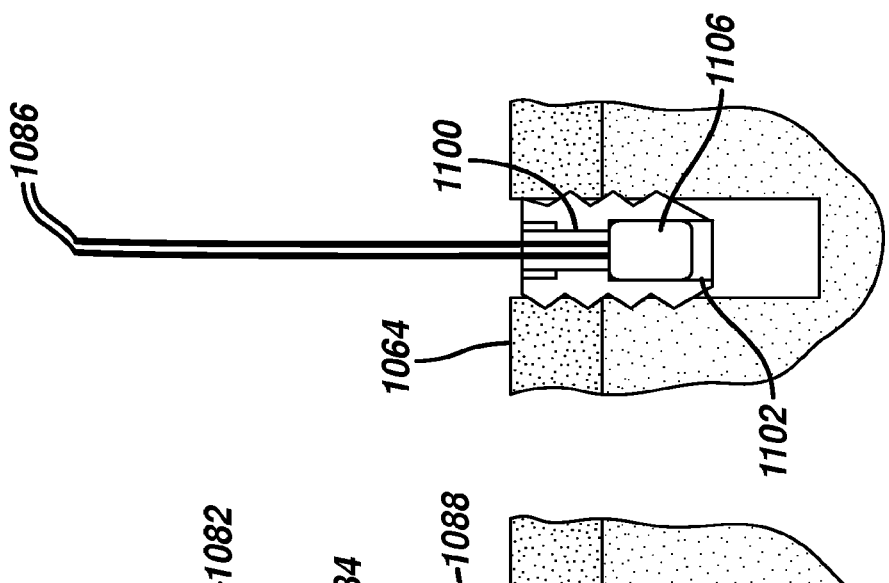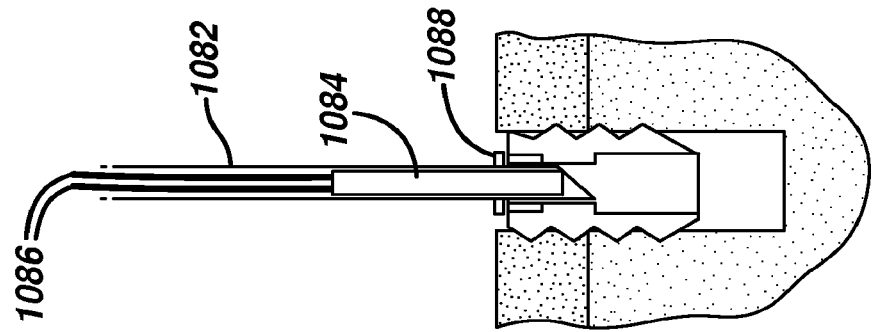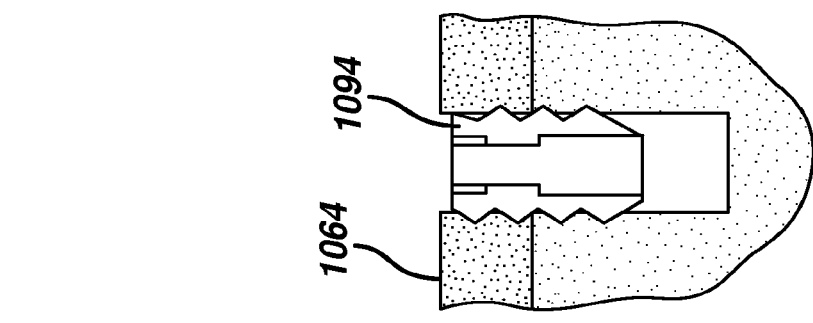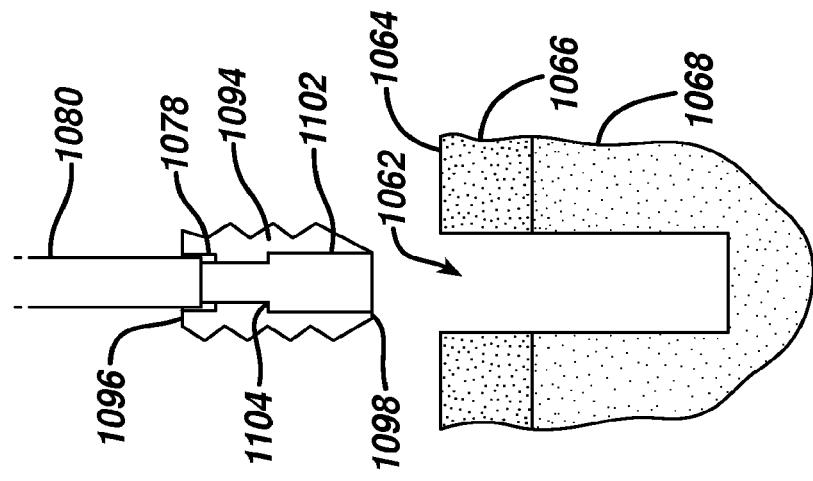

METHODS AND DEVICES FOR REPAIRING AND ANCHORING DAMAGED TISSUE

CROSS-REFERENCE TO RELATED APPLICATIONS

The present application is a continuation of U.S. patent application Ser. No. 14/455,331, filed Aug. 8, 2014, which is a continuation of U.S. patent application Ser. No. 12/509,112, filed Jul. 24, 2009, now U.S. Pat. No. 8,828,053, the entire contents of each of which are incorporated by reference into this application.

TECHNICAL FIELD

The present invention relates in general to devices, systems and methods for repairing and anchoring damaged tissue, and more particularly, to devices, systems and methods for anchoring suture to tissue.

BACKGROUND OF THE INVENTION

Injuries to tissue such as cartilage, skin, muscle, bone, tendon and ligament, frequently require surgical intervention to repair the damage and facilitate healing. Surgical procedures to repair tissue damage are often performed using sutures connected to one or more anchoring device (suture anchor) implanted in or adjacent to the damaged tissue. The sutures can also be passed through or around the tissue according to a variety of surgical techniques to secure the repair. The sutures can also interconnect two or more anchors used to perform the repair. Suture anchors have been fabricated with bodies formed from a variety of materials including nonabsorbable materials such as metals and durable polymers, as well as bioabsorbable materials such as absorbable polymers, bioceramics, absorbable composites and processed bone.

Anchors can be designed for fixation with respect to tissue using external screw threads on an anchor body, an expandable body, toggling action, extendable components such as barbs, or other mechanical retention means. Sutures can be connected through or around suture anchors in a fixed or a sliding manner, for example, using eyelets or other passages in an anchor body, and can be secured using stationary or sliding knots, interference among anchor components, interference between an anchor and surrounding tissue, or other means. Some suture anchors are designed for suture to slide unidirectional through or around the anchor, enabling a surgical repair to be tightened by tensioning a portion of the suture with respect to the anchor. Among their many surgical applications, suture anchors are used with sutures to reattach damaged tendons or ligaments to bone, to tighten compromised tissue surrounding articulating joints, and to repair tears in cartilage, such as torn meniscal cartilage in a knee. In some applications, two or more anchors joined by an adjustable length of suture enable a tissue tear to be cinched closed, or compromised tissue to be stabilized.

Of great importance in suture anchor design is maximizing the retention strength of the anchor in tissue, to minimize the risk of anchor breakage or pullout from tissue when an attached suture is tensioned with respect to the anchor. One common approach to maximizing anchor retention strength is to use physically larger anchors than might be preferable to minimize surgical trauma caused by the procedure used to implant the anchor. Not only does the implantation of a larger anchor generally require a larger and therefore more traumatic surgical incision than would be required to implant a smaller anchor, but the tools required to implant or deploy a larger anchor may also be correspondingly larger. Compounding this issue, the process of deploying an anchor in tissue can require both substantially vertical access to the tissue repair site, and significantly deeper penetration into or through the tissue than the depth required to retain the anchor after deployment in tissue. In addition, many surgical anchors have sharp edges that can cause tissue damage when implanted in a patient. Addressing these concerns is particularly important in the development of minimally invasive surgeries such as arthroscopic procedures that restrict access to an operative site, at least in part to reduce surgical trauma relative to open surgical procedures.

There is a preference among some surgeons for using non-metallic suture anchors rather than metallic suture anchors. While some nonmetallic anchors can provide advantages over metallic anchors with respect to bioabsorbability or radiolucence, many nonmetallic anchors provide significantly lower mechanical strength than metallic anchors, increasing the potential for mechanical failure of the surgical repair during or post-surgery. For example, suture may cut through relatively soft materials used to fabricate a nonmetallic anchor, a process often called "cheese-wiring." With metallic suture anchors, the interface between suture and the anchor must also be carefully designed to protect attached suture from breakage. For example, a metallic suture anchor may require precision polishing to minimize suture failure where suture contacts the much harder metal. With any suture anchor, sharp bends of suture about anchor components are well-known stress points that can lead to failure of a surgical repair. Post-surgical failure of an anchor-based surgical repair during the healing period is of particular concern because uncontrolled fragments of a failed anchor have the potential to cause injury to the patient.

Accordingly, there remains a need for improved suture anchoring devices, systems and methods for repairing damaged tissue that overcome the limitations and disadvantages of known suture anchors. A need also exists for suture anchors, deployment tools and methods that minimize the surgical trauma associated with the implantation of an anchor of any given size.

SUMMARY OF THE INVENTION

The present invention generally provides devices, systems and methods for anchoring suture to tissue. One aspect of the present invention is a method for anchoring a suture length to human tissue. The method comprises the steps of providing a preformed knot configuration to a first portion of the suture length, positioning the preformed knot configuration into an opening in a portion of the human tissue, and expanding the preformed knot configuration in at least one physical dimension to form an anchoring knot, so as to engage the anchoring knot against the tissue. In one embodiment, the preformed knot configuration is reduced in length and increased in a cross-sectional dimension when reconfigured to form the anchoring knot. The anchoring knot can be formed behind a tissue wall, or within bulk tissue, which can be soft tissue or bone.

The preformed knot configuration can be formed from a single line of suture or from joined lines of suture that can be of a single structure and material, or of different structures and materials. In various embodiments, the preformed suture configuration is formed by intertwining portions of suture using any of a variety of methods including, but not limited to chain-knotting, braiding and crocheting. In an embodiment, the step of reconfiguring the preformed knot configuration into an anchoring knot includes placing an abutment against the preformed knot configuration and moving the suture length relative to the abutment to cause the preformed knot configuration to bunch up and increase in cross sectional area as the anchoring knot.

The preformed knot configuration can be delivered to tissue through an inserter tube. In an embodiment, the inserter tube is passed through a tissue wall, and the anchoring knot is formed behind the tissue wall. In one embodiment, the preformed knot configuration does not protrude more than 5 mm beyond the wall before fully forming the anchoring knot. In another embodiment, the diameter of the anchoring knot is at least twice the diameter of the inserter tube.

Another aspect of the present invention is a suture unit for anchoring in human tissue. The suture unit includes a first preformed knot configuration along a portion of a length of suture. The first preformed knot configuration has a maximum diameter along the suture length and is reconfigurable into a first anchoring knot having a minimum diameter that is at least five times larger than the first preformed knot configuration maximum diameter. The first preformed knot configuration can be formed from a single line of suture or from joined lines of suture that can be of a single structure and material, or of different structures and materials. In various embodiments, the preformed suture configuration is formed by intertwining portions of suture, using methods including, but not limited to chain-knotting, braiding and crocheting.

In an embodiment, the first preformed knot configuration includes a portion of suture formed into a loop closed with a sliding knot that in one embodiment is positioned within the first preformed knot configuration. The suture unit can include a second preformed knot configuration expandable into a second anchoring knot.

BRIEF DESCRIPTION OF THE DRAWINGS

The invention will be more fully understood from the following detailed description taken in conjunction with the accompanying drawings, in which:

FIG. 7a and FIG. 7b illustrate an embodiment of a delivery tool of the present invention that can be used to deliver the anchoring device illustrated in FIG. 6a and FIG. 6b to tissue.

FIG. 8a and FIG. 8b illustrate an embodiment of a delivery tool of the present invention including a curved delivery needle.

FIG. 10a and FIG. 10b illustrate an embodiment of a delivery tool of the present invention for single-location anchoring and for daisy-chaining anchoring locations.

FIG. 16a through FIG. 16d illustrate another embodiment of an anchoring system of the present invention wherein a suture head is deployed internally to an intermediate anchoring implant.

DETAILED DESCRIPTION

Figure 1A:
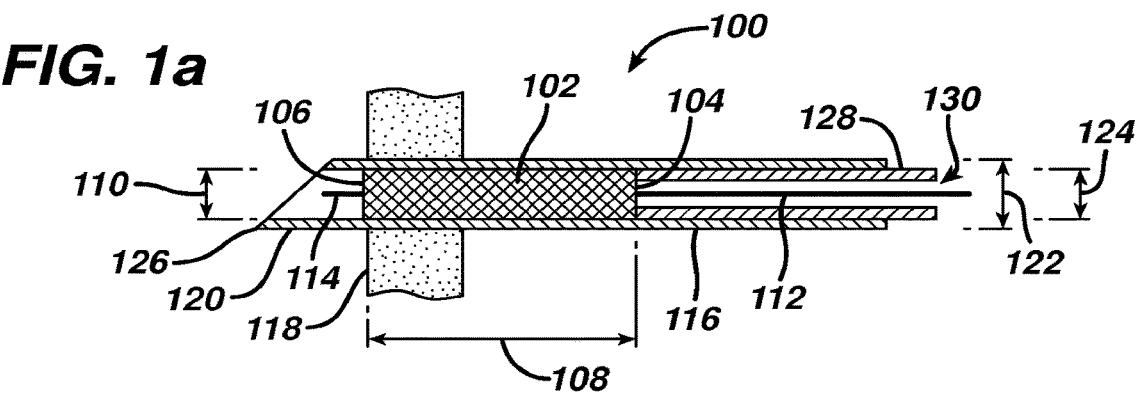
FIG. 1a through FIG. 1d illustrate an embodiment of a suture-anchoring device and its deployment according to the present invention.

Certain exemplary embodiments will now be described to provide an overall understanding of the principles of the structure, function, manufacture, and use of the devices, systems and methods disclosed herein. Those skilled in the art will understand that the devices and methods specifically described herein and illustrated in the accompanying drawings are nonlimiting exemplary embodiments and that the scope of the present invention is defined solely by the claims. The features illustrated or described in connection with one embodiment may be combined with the features of other embodiments. Such modifications and variations are intended to be included within the scope of the present invention. It should be noted that the figures are generally schematic and not drawn to scale, and are intended only to facilitate the description of specific embodiments of the invention.

The present invention generally provides devices, systems and methods for anchoring suture to tissue. The term "tissue" is used herein to refer to any natural body tissue including, but not limited to cartilage, skin, muscle, bone, tendon, ligament and organs, as well as to prosthetic materials such as grafts or other prosthetics that can be repaired or attached to natural body tissues with sutures and anchoring devices. Embodiments of suture anchoring devices fabricated substantially from surgical suture or any elongated, thread-like materials that can be used as medical devices (hereinafter, "suture") are disclosed herein. The suture can comprise a single filament or a plurality of interwoven filaments, and can have any cross-sectional shape including, but not limited to a substantially circular cross section, and a flattened ribbon or tape-like cross section. Further, the suture can be non-absorbable, bioabsorbable, or partially bioabsorbable. Without deviating from the intent or scope of the invention, the suture material can be mechanically or chemically modified, treated or coated to enhance lubricity or knot-holding ability, to elute a medicament, or for any combination of the aforementioned or other therapeutic purposes. Further, although various embodiments of anchoring devices in accordance with the invention can be constructed entirely of suture, additional components such as clips or adhesives can be included without deviating from the intent or scope of the invention.

An anchoring device according to the present invention generally comprises one or more segment of suture (hereinafter, suture tail) extending from an anchoring member having a longitudinally elongated, small cross section initial configuration (hereinafter, a suture head). Upon deployment, the suture head is reconfigured (collapsed) to a longitudinally compressed configuration (an anchoring knot) of correspondingly larger cross-section than the suture head. That is, the anchoring knot has a larger cross sectional area and a larger average cross sectional dimension (hereinafter, cross-sectional dimension) than the corresponding dimensions of the suture head. In some embodiments, for delivery to tissue, the suture anchoring device is disposed in a cannulated delivery needle having an outer diameter substantially smaller than the cross-sectional dimension of the anchoring knot. In general, collapsing a suture head to an anchoring knot is accomplished by tensioning a specific one or more (collapse tail) of the one or more suture tail, with respect to the suture head.

FIG. 1a schematically illustrates an embodiment of a suture-anchoring device 100 according to the present invention. The suture anchoring device 100, illustrated undeployed in FIG. 1a, comprises a suture head 102 having a first head end 104, a second head end 106, a head length 108 therebetween and an undeployed cross-sectional dimension 110 that is smaller than the head length 108. A first suture tail 112 is seen to extend substantially from the first head end 104. In an embodiment, a second suture tail 114 extends substantially from the second head end 106. In a further embodiment, the second suture tail 114 comprises a closed loop of suture extending from the second head end 106. In other embodiments, two or more suture tails extend from one or both of the first 104 and the second head end 106.

The suture head 102 comprises a longitudinally extended, preformed knot configuration, by which we mean any braided, crocheted, woven, knotted or otherwise configured section of suture that, for deployment and fixation with respect to tissue, can be readily collapsed into a longitudinally compressed, expanded cross-section form referred to herein as an anchoring knot.

The suture head 102 is seen to be disposed in a cannulated delivery needle 116 for delivery into or through tissue 118. The delivery needle 116 has a distal delivery end 120, an outer diameter 122 and an inner diameter 124. Further, the delivery needle 116 can be straight or curved along its length. In an embodiment, the delivery end 120 includes a tissue-penetrating point 126. In another embodiment (not illustrated), the delivery end 120 is not pointed. A piston 128 having a longitudinal piston cannulation 130 therethrough is seen to be slidingly disposed within the delivery needle 116, proximal to the suture head 102. The first suture tail 112 is seen to pass proximally from the suture head 102 through the piston cannulation 130.

Figure 1B:
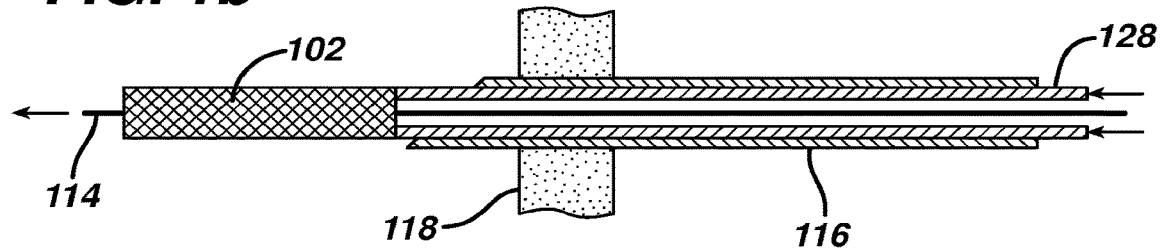

Now referring to FIG. 1b, in one embodiment, the suture head 102 is delivered from the delivery needle 116 to the tissue 118 by pushing the piston 128 distally against the suture head 102 to expel the suture head 102 from the delivery needle 116. The piston 128 is seen to abut the expelled suture head 102. In an embodiment, the piston 128 is coupled to a proximal handle (not illustrated) that provides control of the longitudinal position of the piston 128 within the delivery needle 116. In an alternate embodiment, the suture head 102 is delivered from the delivery needle 116 by distally pulling the second suture tail 114. In one embodiment, the needle 116 is straight. In another embodiment, the needle 116 is curved and the piston 128 is flexible so as to enable the piston 128 to slide along the curve for delivery of the suture head 102 from the needle 116. As the suture head 102 substantially comprises suture, it is also flexible for sliding through a curved needle.

Figure 1C:
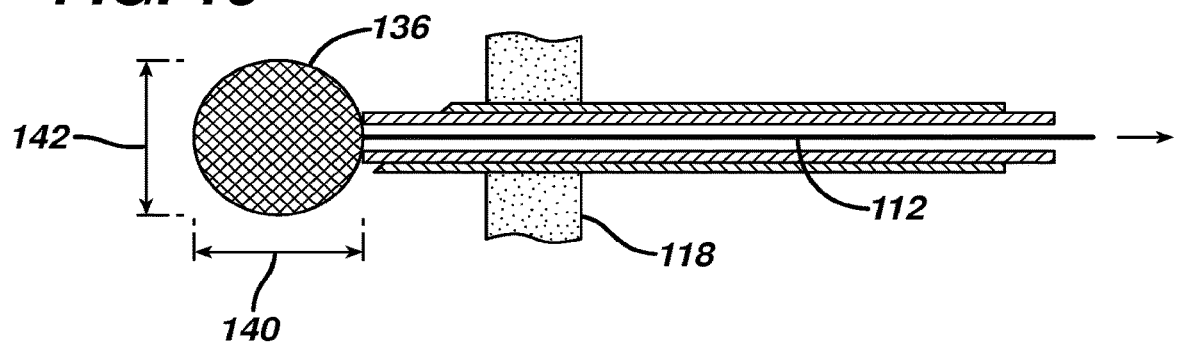

Now referring to FIG. 1c, following or concurrently with delivery of the suture head 102 from the needle 116, the suture head 102 is collapsed to form an anchoring knot 136. In an embodiment, the suture head 102 is collapsed to the anchoring knot 136 by tensioning 138 the first suture tail 112 (a collapse tail) with respect to the suture head 102 after the suture head 102 has been pushed entirely out of the distal end 120 of the needle 116 by the piston 128. The piston 128 abutting the suture head 102 provides a counter force to the tensioning 138 of the first suture tail 112 with respect to the suture head 102, to collapse the suture head 102 to the anchoring knot 136.

The term "collapse tail" is used herein to describe any suture tail that, when tensioned with respect to a suture head, can be used to collapse the suture head to an anchoring knot. The anchoring knot 136 has a knot length 140 that is shorter than the head length 108, and a correspondingly increased cross section 142, determined substantially by the volume of suture originally comprising the suture head 102.

In another embodiment, the first suture tail 112 is tensioned concurrently with the suture head 102 being expelled from the distal end 120 of the needle 116, collapsing the suture head 102 to the anchoring knot 136 as it emerges from the needle 116. In this embodiment, the suture head 102 does not extend distally from the delivery needle 116 the full head length 108 during deployment, but instead extends only the knot length 140. This shallower extension can provide deployment of the anchoring device 100 that minimizes surgical trauma to tissue positioned distally beyond, but in proximity to the distal end of the delivery needle.

Figure 1D:
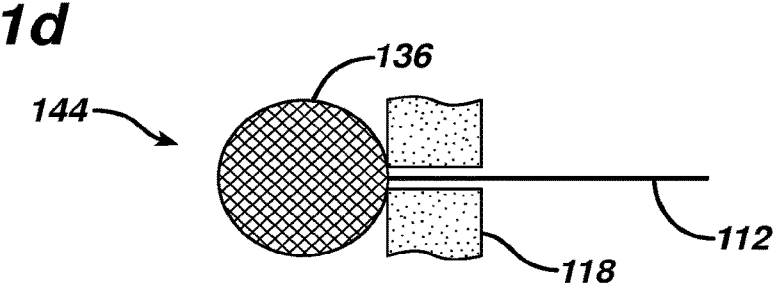

FIG. 1d illustrates a fully deployed anchoring device 144, wherein the needle 116 is seen to have been removed, and the anchoring knot 136 is anchored with respect to the tissue 118, leaving the first suture tail 112 available for connection to tissue or to another anchoring device, or for any other surgical step requiring a suture that is anchored to tissue. According to the requirements of a particular surgical repair, the anchoring knot 136 can be deployed behind a tissue wall as illustrated in FIG. 1d, or within bulk tissue, for example, within a bone for anchoring suture to the bone. In other embodiments, two or more suture heads, interconnected by suture, are disposed in a needle for surgical procedures requiring two or more tissue anchoring points.

The anchoring knot 136 has a knot length 140 that is less than the head length 108, and a deployed cross sectional dimension 142 that is correspondingly greater than the undeployed cross sectional dimension 110, and greater than the outer diameter 122 of the needle 116. In an embodiment, the anchoring knot 136 is amorphous, that is, having an incompletely predetermined external shape following collapse from the suture head 102 to the anchoring knot 136. In general, anchoring knots formed from suture heads according to the various embodiments of the present invention are amorphous. Although neither the suture head 102 nor the anchoring knot 136 have a completely predetermined shape, either can be reasonably described as having a length and a diameter transverse to the length, the diameter approximately defined by the average cross-sectional dimension transverse to the length.

By way of nonlimiting example, in one embodiment, the head length 108 is between approximately ten and fifty times the undeployed cross-sectional dimension 110, and the deployed cross-sectional dimension 142 is between three and ten times the undeployed cross-sectional dimension 110. The suture-anchoring device 100 can be fabricated substantially from a single continuous length of suture, or from a plurality of coupled lengths of suture. The plurality of coupled lengths can include a single type of suture or a combination of suture types and sizes. Further, the one or more suture tail can be fixedly coupled to the anchoring knot, or slidably coupled therethrough. In one embodiment, the inner diameter 124 of the needle 116 is less than about six times a diameter of the suture material from which the suture head is configured. In another embodiment, the inner diameter 124 of the needle 116 is less than about four times a diameter of the suture material from which the suture head is configured.

In an anchoring device according to the present invention, the design of the suture head substantially determines the overall design and procedural details of delivery and deployment. The design of the suture head also determines the pull-out strength of the deployed anchoring knot, and the anchor density, that is, the mass of suture material in an anchoring knot having a given cross-sectional dimension. Many anchoring device designs are possible within the scope of the present invention. For nonlimiting descriptive purposes herein, these designs are grouped into two general categories respectively called non-sliding embodiments, wherein all suture tails extending from a fully deployed anchoring knot are fixed thereto substantially without sliding through the knot, and sliding embodiments, wherein at least one length of suture slidingly passes through the fully deployed anchoring knot. Sliding embodiments are advantageous for some surgical applications, for example, where it is desirable to tension suture between a deployed anchoring member and attached tissue, to draw two or more anchoring devices together to close a tissue tear, or to gather together intervening tissue between anchoring devices.

In an illustrative sliding embodiment, the anchoring device comprises at least a first length of suture and a second length of suture. The first length of suture generally comprises the bulk of a suture head (and, following deployment, a corresponding anchoring knot). The second length of suture comprises two suture tails and is slidable through the anchoring knot by tensioning one or the other of the two tails individually with respect to the anchoring knot. The sliding embodiment can further include additional sliding sutures having corresponding pairs of suture tails. Sliding embodiments can also include one or more fixed suture tail that can comprise a portion of the first length of suture, or an additional length of suture fixedly connected, for example, tied, to the first length of suture. Further, depending on the specific design of the suture head, one or more suture tail can comprise one or both of a collapse tail and a sliding tail.

Nonsliding embodiments can comprise a single length of suture or a plurality of suture lengths that are fixedly joined together, for example, by one or more knots. Nonsliding embodiments include a suture head from which one or more suture tail extends, at least one of the one or more suture tail comprising a collapse tail.

A suture head according to the present invention can comprise any preformed knot configuration that can be collapsed from a longitudinally extended form to a longitudinally compressed, increased cross section anchoring knot. In various embodiments, the suture head includes a plurality of openings comprising loops, penetrations or other openings formed along a first longitudinal section of suture. A second longitudinal section of suture comprising a collapse tail is woven through two or more of the plurality of the openings. One or more suture tails extends from the suture head, at least one of the one or more suture tails comprising the collapse tail. In one embodiment, the first section of suture, the second section of suture and the one or more suture tail comprise a single continuous length of suture. In another embodiment, the first section of suture, the second section of suture and the one or more suture tail comprise two or more joined lengths of suture.

Figure 2A:
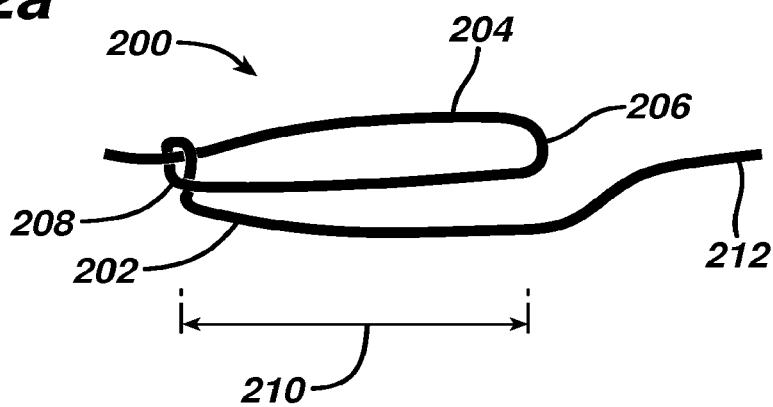
FIG. 2a through FIG. 2d illustrate a nonsliding embodiment of a suture fixation device according to the present invention comprising a twisted braid suture head.
Figure 2B:
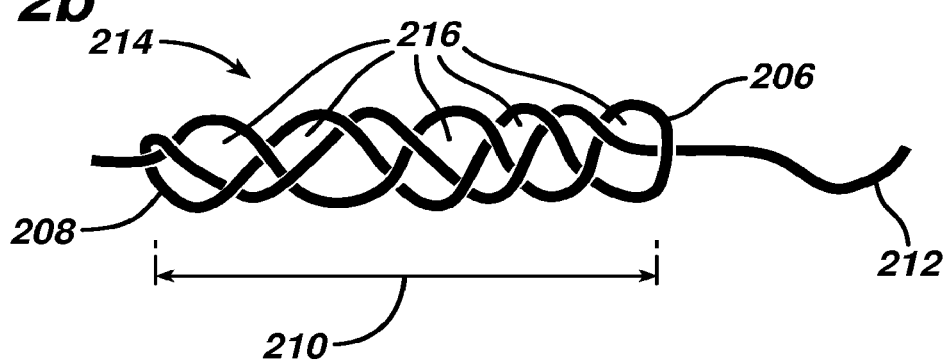

Anchoring devices of the present invention can include one or more of a variety of types of suture heads, and can be fabricated using a variety of methods. One type of suture head comprises a braided section of suture that is collapsible to an anchoring knot. Any type of suture braiding can be used to configure the suture head. An embodiment of a nonsliding, twisted braid suture-anchoring device is schematically illustrated in FIG. 2a and FIG. 2b. FIG. 2a illustrates a first configuration step 200, wherein a length of suture 202 is seen to have been formed into a starting loop 204 having a first head end 206, a second head end 208 and a head length 210 therebetween. A suture tail 212 extends from the second head end 208. FIG. 2b illustrates a configured suture head 214. As can be seen in FIG. 2b, the loop 204 has been repetitively twisted to provide a plurality of openings 216 along the head length 210. Further, the suture tail 212 is seen to have been woven through the plurality of openings 216 from the second head end 208 to the first head end 206, and extends from the first head end 206, where it comprises a collapse tail.

Figure 2C:
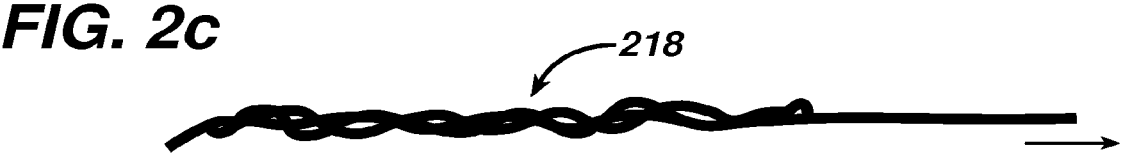
Figure 2D:
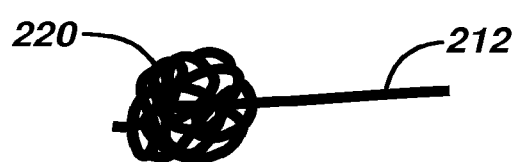

It should be noted that in FIG. 2b, as well as other figures herein detailing suture head configurations, the suture heads are generally illustrated in an expanded schematic form to support description of routing of suture therethrough. Any suture head disclosed herein can be readily compressed in cross section, for example, for disposition within a cannulated delivery needle, as illustrated in FIG. 1a. By way of example, FIG. 2c illustrates the suture head 214 in a compressed cross section form 218, as for disposition in a delivery needle. The suture head 214 can be collapsed to an anchoring knot 220, as illustrated in FIG. 2d, by tensioning the suture tail 212 (collapse tail) with respect to the suture head 214.

By tensioning the first suture tail 212 with respect to the suture head 214, we mean tensioning (pulling) the first suture tail 212 away from the suture head 214, so that the portion of the first suture tail 212 that is woven through the plurality of openings 216 is pulled further through the plurality of openings 216 and through the first head end 206, thereby gathering or bunching the twisted suture along the head length 210 into the anchoring knot 220. For tensioning 222 the first suture tail 212 with respect to the suture head 214, an abutment to the first head end, for example, the piston 128 of FIG. 1 is required to hold the suture head in position for collapsing to the anchoring knot 220. In some embodiments wherein a suture head is embedded in tissue or trapped behind a tissue wall before tensioning a collapse tail, friction with the tissue can also retain the suture head during collapse to an anchoring knot.

Any type and diameter of suture, and any number of openings 216 for braiding or otherwise passing suture therethrough, can be used to configure a suture head according to the present invention. A larger number of openings generally provides a longer suture head and, upon deployment, an anchoring knot having a larger cross sectional dimension, thereby providing greater fixation strength of the anchoring knot with respect to tissue. In one embodiment, a 20 mm long suture head comprises between fifteen and thirty-five openings through which suture can be woven. In another embodiment, the plurality of openings is between twenty and thirty openings. In yet another embodiment, the suture head is approximately 25 millimeters (mm) in length, and upon deployment in tissue, the suture head collapses to a substantially amorphous anchoring knot approximately five mm in diameter.

In one test embodiment, a suture head approximately 20 mm long was configured from partially absorbable, polyethylene-containing braided suture approximately 0.5 millimeters (mm) in diameter (ORTHOCORD™ Orthopaedic Suture from DePuy Mitek, Raynham, Mass.). Deployed through a 2-mm diameter hole into the cancellous layer of artificial bone having a 3-mm thick, 55-durometer cortex, the pullout strength of the resulting anchoring knot was approximately 45 pounds. Deployment of a similarly configured anchoring device through a 2-mm diameter hole in artificial bone having a 3-mm thick, 35-durometer cortex provided a pullout strength of approximately 22 pounds.

A person skilled in the art will appreciate that, within the scope of the present invention, many different methods can be used to configure a suture head having a longitudinally extended configuration that is collapsible to an anchoring knot. Braids, for example, can be formed by a variety of methods and with any number of suture sections braided together, and a suture head configured to include any braiding pattern is within the scope of the present invention. Further, braiding comprises only one of a variety of methods for configuring a suture head according to the present invention. Other methods for configuring a suture head can be adapted, for example, from other textile arts such as crocheting and weaving.

Figure 3A:
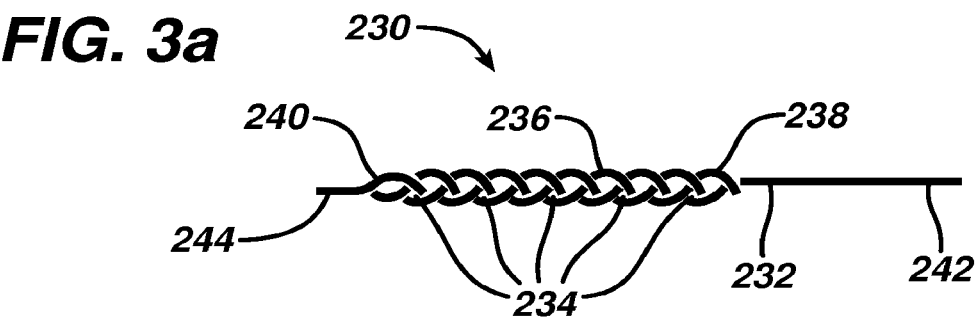
FIG. 3a through FIG. 3c illustrate nonsliding embodiments of suture fixation devices according to the present invention comprising crocheted suture heads.
Figure 3B:
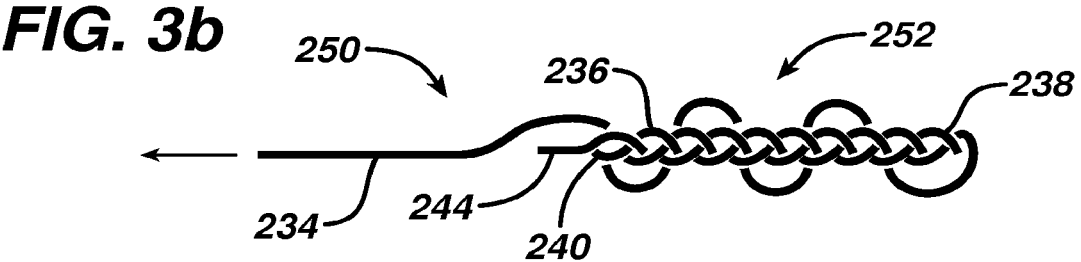
Figure 3C:
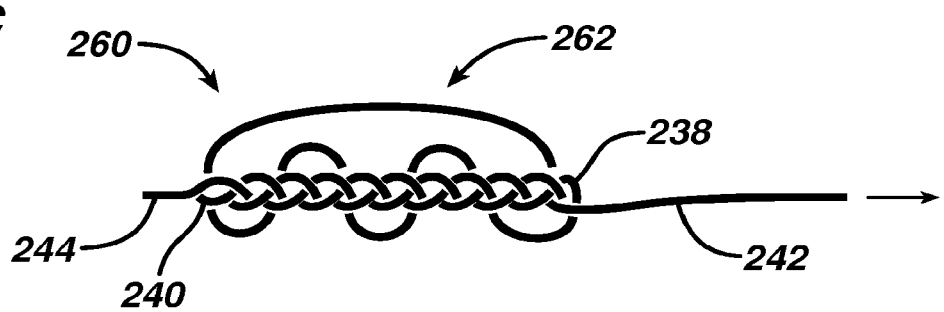

Another anchoring device of the present invention includes a suture head configured using a chain of suture loops. The chain of loops can comprise a plurality of independent suture loops, a physically connected chain of discrete loops, or a plurality of loops formed along a continuous length of suture using known textile arts such as crocheting, where each of the plurality of loops in a chain is formed by pulling a section of the suture through a previously formed loop in the suture. The plurality of loops provides a corresponding plurality of openings through which suture can be woven. Nonsliding embodiments of suture anchoring devices comprising suture heads configured using crocheted suture are schematically illustrated in FIG. 3a through FIG. 3c. FIG. 3a illustrates a crochet configuration step 230 wherein a length of suture 232 has been crocheted to define a plurality of openings 234 along a crocheted section 236 having a first crocheted end 238 and a second crocheted end 240. A first suture tail 242 extends from the first crocheted end 238 and a second suture tail 244 extends from the second crocheted end 240.

FIG. 3b illustrates a first embodiment 250 of a crocheted suture-anchoring device. It comprises a suture head 252 wherein the first suture tail 242 is seen to weave through one or more of the plurality of openings 234 along the crocheted section 236 from the first crocheted end 238 to the second crocheted end 240, and extends from the second crocheted end 240. The suture head 250 can be collapsed to an anchoring knot by tensioning the first suture tail 242 (collapse tail) with respect to the suture head 252.

FIG. 3c illustrates a second embodiment 260 of a crocheted suture-anchoring device. The second embodiment 260 resembles the first embodiment 250, with the addition that in the second embodiment 260, after being woven from the first 238 to the second crocheted end 240, the first suture tail 242 is returned through one or more of the plurality of openings 234 from the second crocheted end 240 to the first crocheted end 238, to extend from the first crocheted end 238. The suture head 262 can be collapsed to an anchoring knot by tensioning the first suture tail 242 (collapse tail) with respect to the suture head 262.

It should be appreciated that not all suture tails are collapse tails. Referring to FIG. 3b and FIG. 3c, in either the first 250 or the second embodiment 260, the second suture tail 244 is directly connected to and extends from the second crocheted end, and tensioning the second suture tail 244 with respect to the respective suture head 252, 262 (providing an abutment against second crocheted end 240 does not collapse the respective suture head to an anchoring knot. Thus the second suture tail 244 can be used, for example, to pull the respective suture head 252, 262, into a cannulated needle, for delivery to tissue or through tissue, without collapsing the respective suture head to an anchoring knot.

Figure 4A:
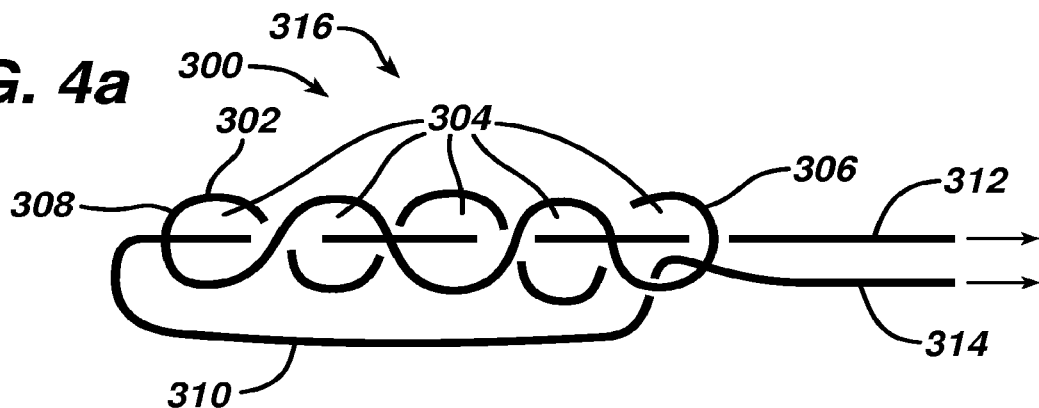
FIG. 4a through FIG. 4d illustrate sliding embodiments of suture anchoring devices according to the present invention.

FIG. 4a through FIG. 4d illustrate sliding embodiments of suture anchoring devices according to the present invention. FIG. 4a illustrates a sliding embodiment of a twisted ring suture-anchoring device 300. The twisted ring suture-anchoring device 300 comprises a suture ring 302 that is a closed ring of suture repetitively twisted to form a plurality of openings 304 between a first twist end 306 and a second twist end 308. A length of suture 310 having a first suture tail 312 and a second suture tail 314 is woven through the plurality of openings 304 between the first twist end 306 and the second twist end 308, and returning through at least one of the plurality of openings 304 near the first twist end 306, to configure a suture head 316 having both the first 312 and the second suture tail 314 extending from the first twist end 306. The suture head 316 can be collapsed to an anchoring knot by simultaneous tensioning of the first 312 and the second suture tail 314 with respect to the suture head 316. Thus the first 312 and the second suture tail 314 comprise collapse tails when tensioned simultaneously with respect to the suture head 316. As can be seen in FIG. 4a, the length of suture 310 is not fixedly connected to the suture ring 302, but woven therethrough to preserve slidability of the length of suture 310 through the anchoring knot. The length of suture 310 can slide through the anchoring knot by individually tensioning either the first 312 or the second suture tail 314 respectively, with respect to the anchoring knot.

A suture ring used to configure a suture head according to the present invention can comprise suture formed as a continuous ring of suture material, or a length of suture closed to form the ring. Any method of closing the length of suture to a ring can be used, including but not limited to knotting, welding, gluing, or crimping with or without a binding clamp or other joining member. Further, the suture ring can include a plurality of substantially parallel strands of suture about its circumference, braided, crocheted, or otherwise interlocked suture. In an embodiment, the suture ring comprises a continuous ring of suture having a first circumference, that is doubled over to form a doubled suture ring having a second circumference that is substantially half the first circumference.

Figure 4B:
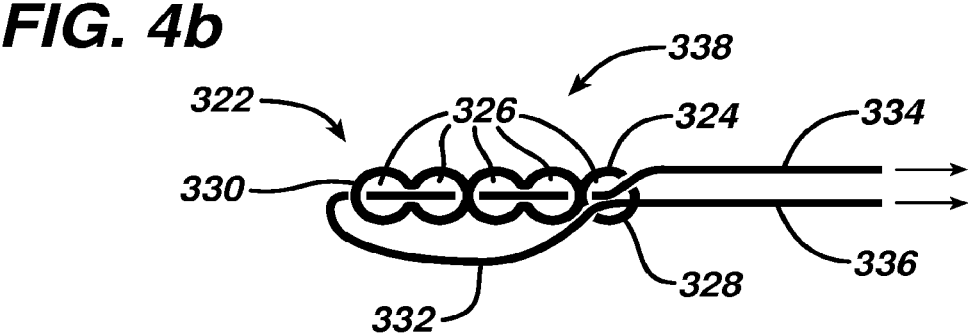

FIG. 4b illustrates a sliding embodiment of a suture-chain suture-anchoring device 322. The suture-chain suture-anchoring device 322 comprises a connected chain of suture rings 324 defining a plurality of openings 326 between a first chain end 328 and a second chain end 330. A length of suture 332 having a first suture tail 334 and a second suture tail 336 is woven through the plurality of openings 326 between the first chain end 328 and the second chain end 330, then returning through at least one of the plurality of openings 326 near the first chain end 328, to configure a suture head 338 having both the first 334 and the second suture tail 336 extending from the first chain end 328. The suture head 338 can be collapsed to an anchoring knot by simultaneous tensioning of the first 334 and the second suture tail 336 with respect to the suture head 338. Thus the first 334 and the second suture tail 336 comprise collapse tails when tensioned simultaneously. As can be seen in FIG. 4b, the length of suture 332 is not fixedly connected to the chain of suture rings 324, but woven therethrough to preserve slidability of the length of suture 332 through the anchoring knot. The length of suture 332 can slide through the anchoring knot by individually tensioning either the first 334 or the second suture tail 336 respectively, with respect to the anchoring knot.

Figure 4C:
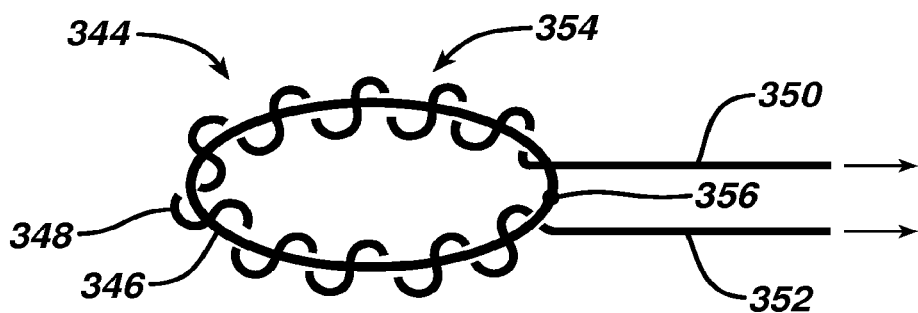

FIG. 4c illustrates a sliding embodiment of a wound-ring suture-anchoring device 344 providing a sliding connection between suture and a deployed anchoring knot. The wound-ring suture-anchoring device 344 comprises a suture ring 346 that can be any type of suture ring described hereinabove. The wound-ring suture-anchoring device 344 also comprises a first length of suture 348 having a first suture tail 350 and a second suture tail 352. The first length of suture 348 is wound substantially helically about the suture ring 346 to configure a suture head 354, with the first 350 and the second suture tail 352 extending from the suture ring 346 substantially adjacent to one another about the circumference of the suture ring 346. In an alternative embodiment, the first length of suture 348 is wound substantially helically about a second length of suture. The second length of suture, with the winding about it, is subsequently joined at a closure point 356 along its length to form the suture ring 346. The suture head 354 can be collapsed to an anchoring knot by simultaneous tensioning of the first 350 and the second suture tail 352 with respect to the suture head 354. Thus the first 350 and the second suture tail 352 comprise collapse tails when tensioned simultaneously. The first length of suture 348 can slide through the anchoring knot by individually tensioning either the first 350 or the second suture tail 352 respectively, with respect to the anchoring knot.

Figure 4D:
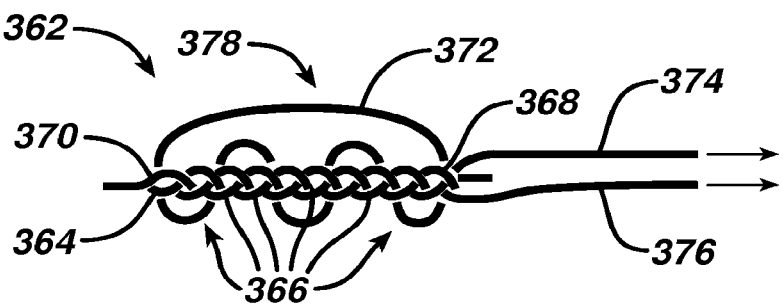

A sliding embodiment of a crochet-type suture-anchoring device 362 is illustrated in FIG. 4d. The crochet-type suture-anchoring device 362 comprises a crocheted section of suture 364 defining a plurality of openings 366 between a first crocheted end 368 and a second crocheted end 370. The crocheted section 364 is similar to the crocheted section 236 described in association with FIG. 3a. The crochet-type suture-anchoring device 362 also comprises a first length of suture 372 having a first suture tail 374 and a second suture tail 376.

As can be seen in FIG. 4d, to configure a suture head 378, the first length of suture 372 is woven through one or more of the plurality of openings 366 between the first crocheted end 368 and the second crocheted end 370, and returned to the first crocheted end 368 through at least one of the plurality of openings 366 near the first crocheted end 368. The first 374 and the second suture tail 376 extend from the first crocheted end 368. In one embodiment, the fraction of the plurality of openings comprises approximately every third opening of the plurality of openings 366. In another embodiment, the first length of suture 372 is woven through substantially each of the plurality of openings 366. In other embodiments, the interval varies along the plurality of openings 366 between the first crocheted end 368 and the second crocheted end 370. In yet another embodiment, the first length of suture 372 passes through a single one of the plurality of openings 366, the single one of the plurality of openings 366 functioning as an eyelet through which the first length of suture 372 passes.

A person skilled in the art will appreciate that any number of additional lengths of suture can be independently woven through one or more of the plurality of openings, thereby providing an anchoring device having a plurality of suture legs extending therefrom (a multisuture anchoring device). In various embodiments, two, three or four lengths of suture are each woven through one or more of the plurality of openings, providing anchoring devices respectively comprising four, six, or eight legs of suture extending therefrom. In some surgical situations it can be desirable to increase the number of sutures connected to a deployed anchoring device. In such circumstances, one or more suture needle with attached suture can be passed through a deployed anchoring knot to provide a multisuture anchoring device.

The suture head 378 can be collapsed to an anchoring knot by simultaneous tensioning of the first 374 and the second suture tail 376 with respect to the suture head 378. Thus the first 374 and the second suture tail 376 comprise collapse tails when tensioned simultaneously with respect to the suture head 378. The first length of suture 372 can slide through the anchoring knot by individually tensioning of either the first 374 or the second suture tail 376 respectively, with respect to the anchoring knot.

FIG. 5a through FIG. 5d illustrate embodiments of suture anchoring devices comprising interpenetrating suture. A suture head according to these embodiments comprises a plurality of longitudinally distributed, substantially transverse penetrations through the material of a first section of suture, and a second section of suture woven through the plurality of penetrations. The plurality of penetrations can comprise any type of penetrations. In one embodiment, the plurality of penetrations is defined using a sharp instrument such as a sewing or suturing needle connected to a suture tail. In another embodiment, the plurality of penetrations comprises a plurality of slits or bores is formed through the suture material to enable weaving of a suture tail therethrough. In yet another embodiment, a plurality of preformed penetrations is provided during fabrication of the section of suture. In still another embodiment, the suture itself comprises a braided material, for example, a braided suture, and the plurality of penetrations pass through the braid at a corresponding plurality of locations.

Figure 5A:
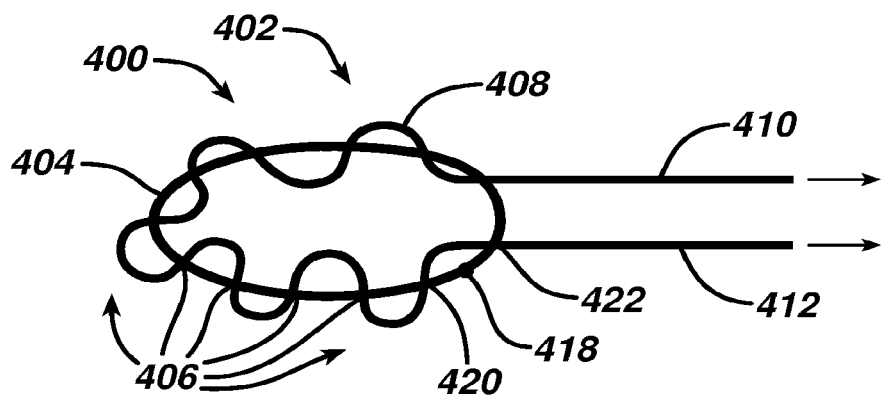
FIG. 5a through FIG. 5d illustrate embodiments of suture anchoring devices according to the present invention comprising interpenetrating suture.
Figure 5B:
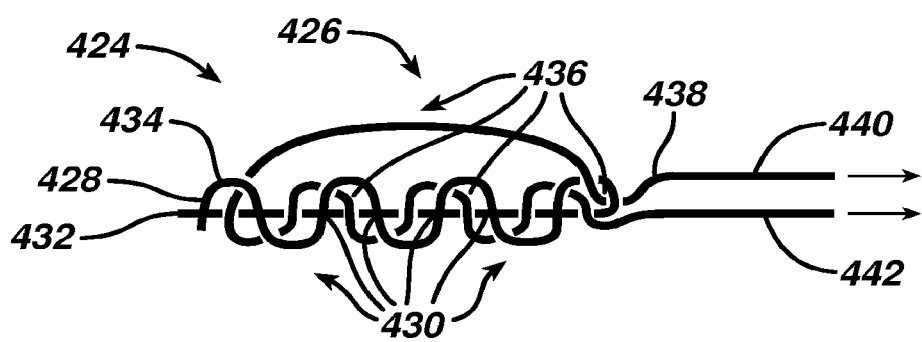

FIG. 5a and FIG. 5b illustrate interpenetrating sliding embodiments. FIG. 5a illustrates a first interpenetrating sliding embodiment 400 of a suture anchoring device wherein a suture head 402 comprises a suture ring 404 having a plurality of penetrations 406 distributed around its circumference. The suture ring 404 can be any type of suture ring disclosed herein. The suture head 402 further comprises a first length of suture 408 woven through the plurality of penetrations 406, and terminating in a first suture tail 410 and a second suture tail 412, each extending from the suture head 402 substantially adjacent to one another about the circumference of the suture ring 404. The suture head 402 can be collapsed to an anchoring knot through which the first length of suture 408 can slide after the anchoring knot is formed, by simultaneously tensioning the first 410 and the second suture tail 412 with respect to the suture head 402. Thus the first 410 and the second suture tail 412 comprise collapse tails when tensioned simultaneously. The first length of suture 408 can slide through the anchoring knot by individually tensioning either the first 410 or the second suture tail 412 respectively, with respect to the anchoring knot.

In an alternate embodiment, the suture ring 404 comprises a second length of suture that is open at a point 418 on the circumference, and the ring shape is maintained by the adjacent penetrations 420, 422 of the second length of suture by the first length of suture 408. In a further alternate embodiment, the second length of suture penetrates the first length of suture, instead of the first length of suture 408 penetrating the second length of suture.

FIG. 5b illustrates a second interpenetrating sliding embodiment 424 of a suture anchoring device wherein a suture head 426 comprises a first length of suture 428 having a plurality of penetrations 430 along a first portion 432 of its length, through which a second portion 434 of the length passes to define a corresponding plurality of openings 436. The suture head 426 further comprises a second length of suture 438 woven through the plurality of openings 436, and terminating in a first suture tail 440 and a second suture tail 442, each extending from the suture head 426. The suture head 426 can be collapsed to an anchoring knot through which the second length of suture 438 can slide, by simultaneously tensioning the first 440 and the second suture tail 442 with respect to the suture head 426. Thus the first 440 and the second suture tail 442 comprise collapse tails when tensioned simultaneously. The second length of suture 438 can slide through the anchoring knot by individually tensioning either the first 440 or the second suture tail 442 respectively, with respect to the anchoring knot.

Figure 5C:
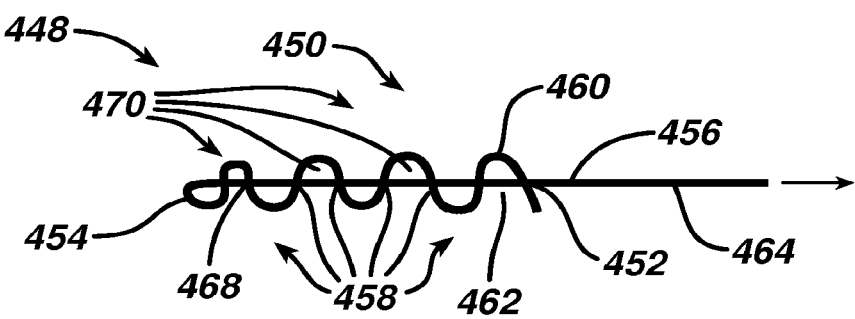
Figure 5D:
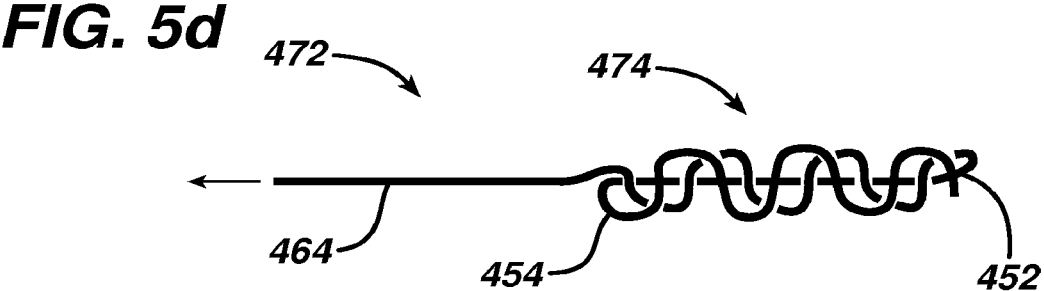

FIG. 5c and FIG. 5d illustrate interpenetrating suture nonsliding embodiments of suture anchoring devices. FIG. 5c illustrates a first interpenetrating nonsliding embodiment 448 wherein a suture head 450 having a first head end 452 and a second head end 454 comprises a first length of suture 456 having a plurality of penetrations 458 along a first portion 460 of its length between the first head end 452 and the second head end 454. A second portion 462 of the length passes through the plurality of penetrations 458 and extends from the first head end 452 as a suture tail 464. The suture head 450 can be collapsed to an anchoring knot by tensioning the suture tail 464 with respect to the suture head 450. In an embodiment, one of the penetrations 468 of the second portion 462 through the first portion 454 is reinforced by knotting or by another means to prevent the suture head from unraveling during deployment. The plurality of penetrations 458 is seen to define a plurality of openings 470 along the suture head 450 between the first head end 454 and the second head end 456.

FIG. 5d illustrates a second interpenetrating nonsliding embodiment 472. The second nonsliding embodiment 472 comprises a suture head 474 that resembles the suture head 450 of FIG. 5c, with the addition that in the second embodiment 472, the suture tail 464 is seen to be reversed in direction and additionally woven through one or more of the plurality of openings 470, to extend from the second head end 454. This additional pass of the suture tail 464 provides a larger volume of suture material in the suture head 474 of the second embodiment 472, compared with the volume of suture material in the suture head 450 of the first embodiment 448. A larger volume of suture in a suture head provides a correspondingly larger anchoring knot upon deployment in tissue. The suture head 474 can be collapsed to an anchoring knot by tensioning the suture tail 464 with respect to the suture head 474.

Although sliding and nonsliding embodiments are generally discussed separately hereinabove, various nonsliding embodiments can be converted to sliding embodiments by passing an additional length of suture through an opening in a nonsliding suture head before deployment. For example, with reference to FIG. 1, in an embodiment where the second suture tail 114 comprises a closed loop of suture, passing a length of suture through the loop before delivering the anchoring device 100 to tissue provides a sliding embodiment of the suture anchoring device, as the passed length of suture will be slidable with respect to the anchoring knot 136. In addition, various sliding embodiments can be converted to nonsliding embodiments, for example, by tying a knot in one or more sliding suture tail.

A person skilled in the art will appreciate that many variations of the suture anchoring devices disclosed herein are within the scope of the present invention, including but not limited to variations in suture material, size, number and combinations of suture lengths used to construct the anchoring device, the number of openings through which suture comprising a collapse tail passes along a suture head, and the number of sliding and nonsliding suture tails extending from a suture head. Further, any number of suture anchoring devices can be coupled together by suture to provide multi-point anchoring systems.

Figure 6A:
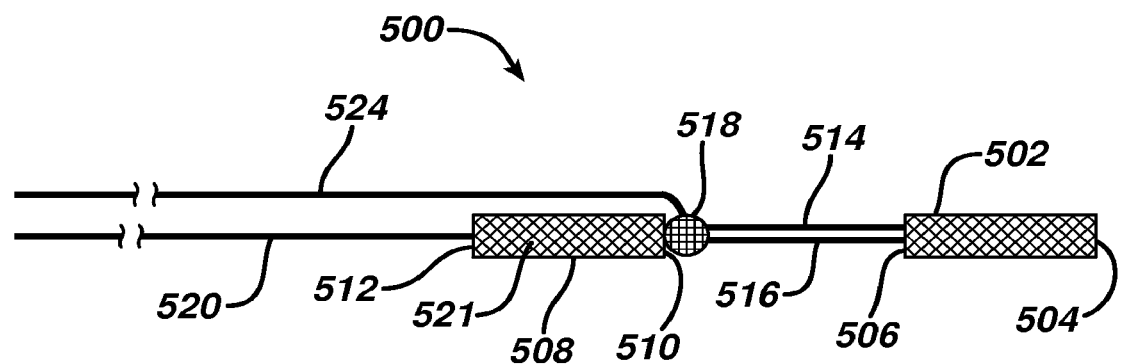
FIG. 6a and FIG. 6b illustrate an embodiment of a suture anchoring device applicable to repairing a meniscus in a knee according to the present invention.

One application of the suture anchoring devices disclosed herein is the repair of a meniscal tear in a knee. FIG. 6a illustrates an embodiment of a dual anchoring device 500 according to the present invention that in one embodiment is used for repairing torn meniscal tissue. The dual anchoring device 500 comprises a first suture head 502 having a first distal end 504 and a first proximal end 506, and a second suture head 508 having a second distal end 510 and a second proximal end 512. The second suture head 508 is seen to be positioned proximal to the first suture head 502. The first suture head 502 is a sliding suture head that can be any type of sliding suture head disclosed herein, or another sliding suture head. In one embodiment, the first suture head 502 is a crochet-type sliding suture head similar to the suture head 378 described in association with FIG. 4d. The first suture head 502 comprises two distal collapse tails 514, 516 that are seen to extend from the first proximal end 506 toward the second suture head 508. The two distal collapse tails 514, 516 comprise a continuous length of suture that passes through the first suture head 502. Together, the two distal collapse tails 514, 516 comprise a suture bridge between the first 502 and the second suture head 508.

The second suture head 508 is a non-sliding suture head that can comprise any type of nonsliding suture head disclosed herein, or another nonsliding suture head. In one embodiment, the second suture head 508 resembles the crochet-type nonsliding suture head 252 described in association with FIG. 3c, with the addition of an integrated sliding knot 518 extending from the second distal end 510. The second suture head 508 also comprises a proximal collapse tail 520 extending proximally from the second proximal end 512. In one embodiment, the second suture head 508, the sliding knot 518, and the two distal collapse tails 514, 516 comprise a single continuous length of suture. In another embodiment, the sliding knot 518, rather than extending from the second distal end 510, is disposed at a location 521 between second distal end 510 and a second proximal end 512 along the second suture head 508.

Figure 6B:
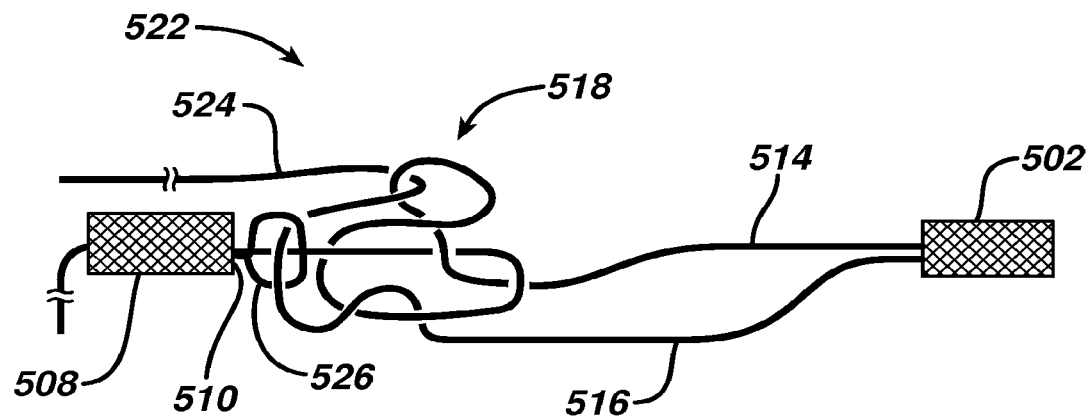

A partially expanded view 522 of the dual anchoring device 500 is shown schematically in FIG. 6b, illustrating the configuration of an embodiment of the sliding knot 518. A first one 514 of the two distal collapse tails 514, 516 is seen to substantially comprise one portion of the sliding knot 518, and to connect to (or be continuous with) the second suture head 508 at the second distal end 510. The second distal collapse tail 516 is seen to pass through the sliding knot to extend proximally from the sliding knot 518, continuous with a tensioning tail 524. The second collapse tail 516 is also seen to pass through a suture loop 526 integral with the second suture head 508 and extending distally therefrom.

An embodiment of a dual suture head delivery tool 530 for delivering the dual anchoring device 500 to tissue is schematically illustrated in FIG. 7a in a cross-sectional view 532 and in FIG. 7b in an external view 534. The dual head delivery tool 530 is seen to comprise a cannulated delivery needle 536 having a distal needle end 538, a proximal needle end 540 and a longitudinal needle cannulation 542 therebetween. The delivery needle 536 is proximally coupled to a cannulated handle 544 having a handle wall 546 and a substantially cylindrical handle cannulation 548, the needle cannulation 542 being continuous with the handle cannulation 548. In an embodiment, the needle 536 is proximally reinforced by a stiffening member 550.

A cannulated piston 552 having a distal piston end 554, a proximal piston end 556 and a longitudinal piston cannulation 557 therebetween, is seen to be disposed slidably within the needle cannulation 542, and to extend proximally into the handle cannulation 548. In one embodiment, each of the needle 536 and the piston 552 is straight. In another embodiment, the needle 536 comprises one or more curve between the distal needle end 538 and the proximal needle end 540, and the piston is flexible enough to be pushed and pulled slidingly through the needle cannulation 542. In one embodiment, the piston 552 comprises a flexible tube. In another embodiment, the piston 552 comprises a flexible, substantially helical coil.

A piston positioning member 558 is fixedly connected to the piston 552, and slidably disposed within the handle cannulation 548. In one embodiment, the positioning member 558 is an annular member disposed about the piston 552. In an embodiment, the piston positioning member 558 substantially irreversibly locks in position longitudinally when maximally advanced distally within the handle cannulation 548. Any means of locking the piston positioning member 558 can be used. In one embodiment, the piston positioning member 558 and the handle 544 comprise interlocking latching members 560, 562 to lock the piston positioning member 558 distally within the handle 544.

A control member 564 is connected to the positioning member 558, for positioning the piston 552 longitudinally within the dual head delivery tool 530, from outside the delivery device. For illustrative purposes, the control member is shown rotated ninety degrees about a longitudinal axis of the tool 530 in FIG. 7a with respect to FIG. 7b. The control member 564 extends laterally outward from the positioning member 558, through a slotted opening 566 in the handle wall 546. The slotted opening 566 can have any configuration that accommodates the requirements an anchoring device disposed in the delivery device, and corresponding surgical delivery requirements. In one embodiment, as illustrated in FIG. 7a and FIG. 7b for delivering the dual anchoring device 500 to tissue, the slotted opening 566 is substantially H-shaped. In an embodiment, the H-shaped opening includes first and second longitudinal slots 812, 814 having respective longitudinal positions that differ from one another along the handle wall 546, each of the two slots being adapted by its respective position for delivery of one of the first 502 and the second suture head 508 from the delivery needle 536. In other embodiments, the slotted opening is substantially T-shaped, L-shaped, longitudinally linear, or has another configuration, respective configurations being adapted to accommodate various suture head delivery requirements In another embodiment, the slotted opening comprises means for locking the piston positioning member 558 distally in the handle cannulation 548.

The control member 564 can comprise any means for communicating one or both of longitudinal and circumferential positioning force to the positioning member 558 and thereby to the piston 552. In one embodiment, the control member 564 is a shaft fixedly connected to the positioning member 558 through the slotted opening 566. In another embodiment, the control member 564 includes means to releasable prevent the piston from moving within the dual head delivery tool 530. In one embodiment, the control member 564 is a thumbscrew that is threaded into the positioning member 558 through the slotted opening 566, such that rotation of the thumbscrew can be used to selectively lock and unlock the position of the piston within the dual head delivery tool 530. In another embodiment, the control member 564 is resiliently loaded with respect to the handle wall 546 to provide a predetermined resistance to movement of the control member 564 along the slotted opening 566.

The dual anchoring device 500 is seen to be disposed within the dual head delivery tool 530, substantially within the needle cannulation 542, distal to the piston distal end 554. The second collapse tail 520 and the tensioning tail 524 pass proximally from the dual anchoring device 500 through the piston cannulation 557. Proximal to the piston proximal end 556, the tensioning tail 524 terminates at a tensioning tail end 568 and the second collapse tail 520 terminates at a second collapse tail end 570. The second collapse tail 520 also comprises a releasable holding member 572 disposed proximally to the proximal piston end 556, outside the piston cannulation 557. The releasable holding member 572 prevents the second collapse tail 520 from sliding distally through the cannulation of the piston 552. In one embodiment, the releasable holding member 572 is a releasable clamp attached to the second collapse tail 520. In another embodiment, the releasable holding member 572 is a releasable knot in the second collapse tail 520. In a further embodiment, proximally tensioning the second collapse tail 520 releases the releasable knot. Upon release of the releasable holding member 572, the second collapse tail 520 can slide distally through the cannulation of the piston 552.

The control member 564 controls the longitudinal position of the distal end of the piston 552 within the delivery needle 536, and thereby controls the expulsion of the dual anchoring device 500 from the delivery needle 536. Depending on the configuration and longitudinal position of the slotted opening 566, the control member 564 can be used to selectively expel only the first suture head 502 from the delivery needle 536 for a predetermined surgical step, and selectively expel the second suture head 508 for a later surgical step, thus enabling multipoint anchoring procedures using devices and methods of the present invention.

It can be advantageous, particularly for a delivery device comprising a curved delivery needle, to be able to rotate the handle about a longitudinal axis with respect to the curved needle, to facilitate access to a control member on the handle for a particular procedure, or to accommodate differing preferences between left and right handed surgeons. An embodiment of a curved needle delivery tool 574 is illustrated in FIG. 8a. The curved needle delivery tool 574 generally resembles the dual head delivery tool 530 associated with FIG. 7a and FIG. 7b, which comprises a straight delivery needle. The curved needle embodiment 574 includes a cannulated curved delivery needle 576 having a distal delivery end 578 and a proximal end 580 that is rotatably coupled to a handle 584 about a common longitudinal axis 586. A control member 588 is accessible on an outside surface 590 of the handle 584. The curved delivery needle 576 further comprises one or more curved portion 592, distal of which the curved needle 576 deviates from the axis 586.

In an embodiment, the curved needle delivery tool 574 comprises a plurality of preferred relative rotational orientations about the axis 586 between the handle 584 and the curved needle 576. In a further embodiment, the plurality of preferred orientations comprises a plurality of detents 594 circumferentially distributed about the circumference of one or both of the handle 590 and the curved needle 576. In another embodiment, angular markings are provided on one or both of the handle 584 and the curved needle 576 to indicate the relative rotational orientation between the curved needle 576 and the handle 584. FIG. 8a illustrates the curved needle delivery tool 574 in a first angular orientation 596 between the handle 584 and the curved needle 576. FIG. 8b illustrates the curved needle delivery tool 574 in a second angular orientation 598 between the handle 584 and the curved needle 576.

FIG. 9a through FIG. 9k schematically illustrate a surgical repair procedure for a torn meniscus in a knee using the dual anchoring device 500 illustrated in FIG. 6 and the dual head delivery tool 530 illustrated in FIG. 7. The procedure can be performed arthroscopically or as an open surgical procedure. Before beginning the procedure, the patient is prepared according to known preparatory and surgical techniques including the provision of access to the torn meniscus. The following description of the procedure references FIG. 6 and FIG. 7 as well as FIG. 9a through FIG. 9n. Each of FIG. 9a through FIG. 9n includes an illustration of a surgical step, in some of the figures accompanied by an illustration representing a position of the control member 564 in the substantially H-shaped slotted opening 566 as illustrated in FIG. 7.

Figure 9A:
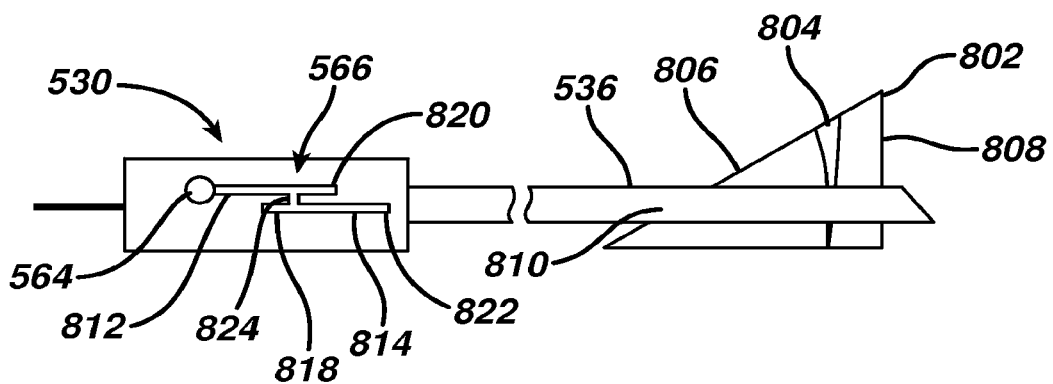
FIG. 9a through FIG. 9k illustrate an embodiment of a surgical repair procedure of the present invention, for repairing a torn meniscus in a knee.

FIG. 9a illustrates a first step in which the delivery needle 536 of the dual head delivery tool 530 is seen to have been passed through a meniscus 802 that has suffered a meniscal tear 804. The meniscus 802 is seen to have a first meniscal surface 806 which faces toward a femur (not shown) and a second meniscal surface 808 which faces laterally or medially away from the femur. It is preferred to minimize the protrusions on the first surface 806 facing the femur to minimize irritation etc. of such surface which bears a load from the femur. The delivery needle 536 is seen to have penetrated the meniscus 802 at a first location 810, entering through the first meniscal surface 806, and exiting through the second meniscal surface 808. The first location 810 is determined by the surgeon performing the procedure, to optimize closure of the meniscal tear 804. In one embodiment, the delivery needle 536 penetrates through the meniscus 802 across the meniscal tear 804.

The H-shaped slotted opening 566 is seen to comprise a first longitudinal channel 812 and a second longitudinal channel 814, each having a respective proximal end 816, 818 and distal end 820, 822. The H-shaped slotted opening 566 further comprises a bridging channel 824 interconnecting the first 812 and the second channel 814. The control member 564 is seen to be positioned at the proximal end 816 of the first channel 812. In this position of the control member 564, the dual anchoring device 500 is maximally retracted into the delivery needle 536.

Figure 9B:
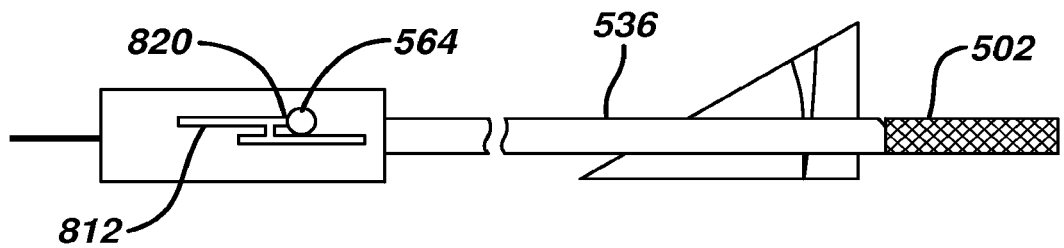
Figure 9C:
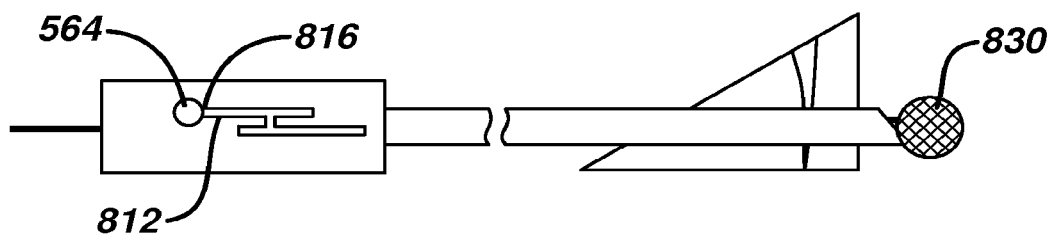

Now referring to FIG. 9b, in a second step, the control member 564 is seen to have been repositioned to the distal end 820 of the first channel 812, thereby expelling the first suture head 502 distally from the delivery needle 536. The first channel 812 does not extend distally far enough to expel the second suture head 508 from the delivery needle 536. Now referring to FIG. 9c, in a third step, the control member 564 is seen to have been retracted to the proximal end 816 of the first channel 812. The retraction of the control member 564 collapses the first suture head 502 to a first anchoring knot 830 as the proximal piston end 556 bears against the releasable holding member 572, transmitting tension via the proximal collapse tail 520, the second suture head 508, and the two distal collapse tails 514, 516 to the first suture head 502.

Figure 9D:
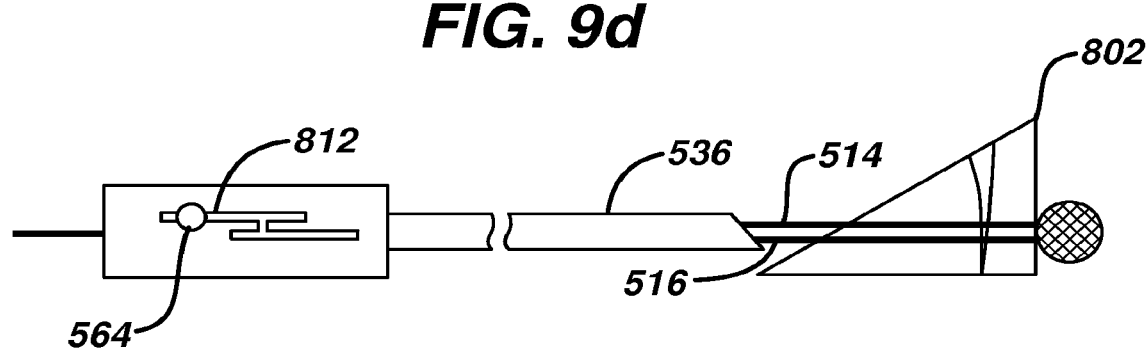

Now referring to FIG. 9d, in a fourth step, the delivery needle 536 is seen to have been retracted from the meniscus 802, leaving the two distal collapse tails 514, 516 bridging between the first anchoring knot 830 and the second suture head 508 within the delivery needle 536. In an embodiment, retracting the delivery needle 536 positions the first anchoring knot 830 proximally against the second meniscal surface 808. The control member can move somewhat distally in the first longitudinal channel 812 as the delivery needle 536 is retracted from the meniscus 802.

Figure 9E:
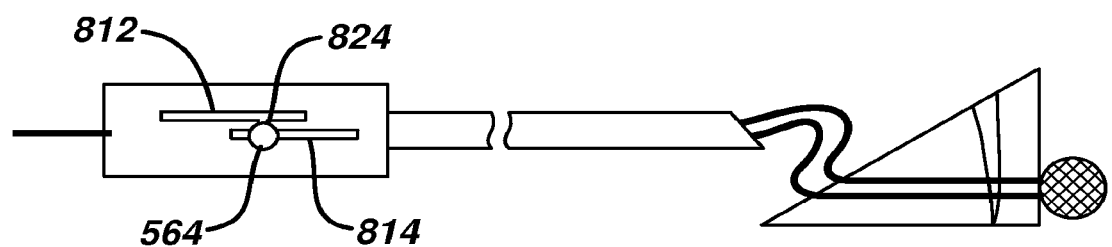
Figure 9F:
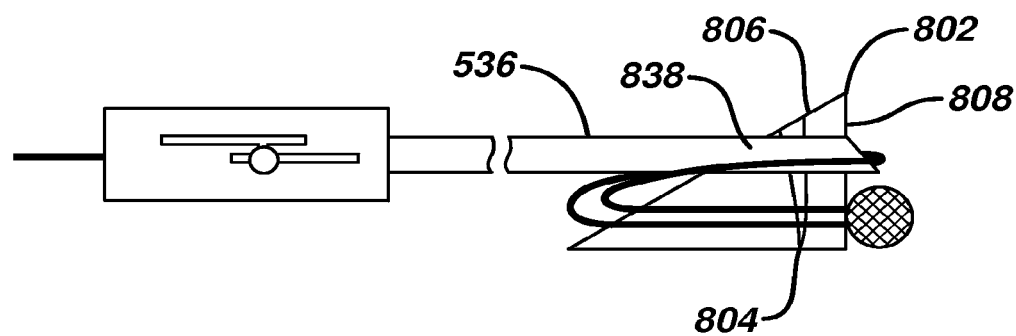

Now referring to FIG. 9e, in a fifth step, the control member 564 is seen to have been moved distally in the first longitudinal channel 812 and repositioned into the second longitudinal channel 814 via the bridging channel 824. Now referring to FIG. 9f, in a sixth step, the delivery needle 536 is seen to have been passed through the meniscus 802 at a second location 838, entering through the first meniscal surface 808, and exiting through the second meniscal surface 808. The second location 838 is determined by the surgeon to optimize closure of the meniscal tear 804. In one embodiment, the delivery needle 536 penetrates through the meniscus 802 across the meniscal tear 804.

Figure 9G:
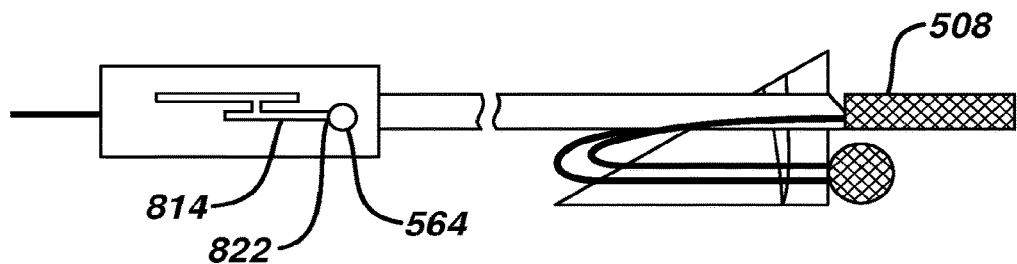
Figure 9H:
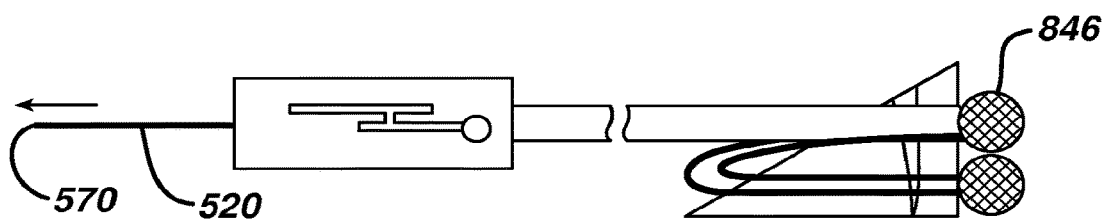

Now referring to FIG. 9g, in a seventh step 840, the control member 564 is seen to have been moved to the distal end 822 of the second longitudinal channel 814, thereby expelling the second suture head 508 from the delivery needle 536 and locking the longitudinal position of the positioning member 558 and the piston 552. Now referring to FIG. 9h, in an eighth step 842, the second collapse tail 520 is tensioned 844 proximally to collapse the second suture head 508 to a second anchoring knot 846. In addition, the releasable holding member 572 is released in this step. In one embodiment, the releasable holding member 572 is a knot in the second collapse tail, and tensioning the second collapse tail 520 releases the knot, leaving the second collapse tail end 570 free to pass through the piston cannulation 557.

Figure 9I:
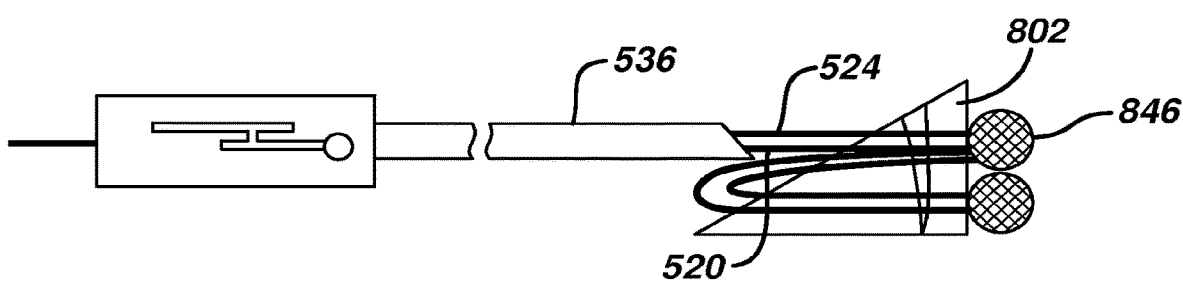
Figure 9J:
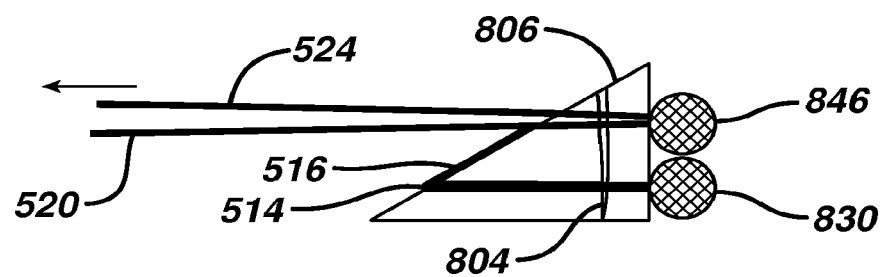
Figure 9K:
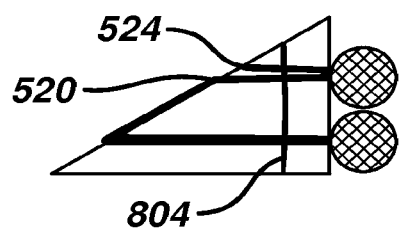

Now referring to FIG. 9i, in a ninth step 848, the delivery needle 536 is seen to have been retracted from the meniscus 802, leaving the second collapse tail 520 and the tensioning tail 524 extending through the meniscus 802 and between the second anchoring knot 846 and the delivery needle 536. Now referring to FIG. 9j, in a tenth step 850, the dual head delivery tool 530 is seen to have been removed entirely from the surgical site, leaving the second collapse tail 520 and the tensioning tail 524 extending from the second anchoring knot 846 and through the first meniscal surface 806. Further, proximally tensioning 852 the tensioning tail 524 transmits tension in turn through the slipknot 518 (now part of the second anchoring knot 846) to the second distal collapse tail 516, through the first anchoring knot 830 and to the first distal collapse tail 514, thereby shortening the suture between the first 830 and the second anchoring knot 846, to close the meniscal tear 804. Now referring to FIG. 9k, in an eleventh step 854, the second collapse tail 520 and the tensioning tail 524 are seen to have been trimmed to or below the first meniscal surface 806, resulting in a repaired meniscal tear 804.

In an alternate embodiment, one or both of the tensioning tail 524 and the second collapse tail 520 is left untrimmed, and is passed through a closed loop of suture extending distally from an additional suture head, to provide an additional "daisy-chained" suture anchoring point when the additional suture head is delivered to tissue. In one embodiment, the additional suture head is the suture head 102 of FIG. 1, wherein the second suture tail 114 comprises the closed loop of suture extending distally from the second head end 106. Any number of additional anchoring points can be provided by this daisy-chaining process, as each deployed anchoring knot comprises at least one suture tail that can be passed through a suture loop of yet another suture head, for anchoring to tissue.

One skilled in the art will appreciate that the embodiments illustrated hereinabove of dual suture anchoring devices, associated delivery tools and surgical methods, are readily adapted for single-point, and for other multi-point anchoring embodiments. In one embodiment, a single suture head is disposed in a delivery needle for deployment of a single anchoring knot to tissue. In another embodiment, three suture heads are disposed in a delivery needle, for sequential deployment to tissue as anchoring knots. In yet another embodiment, one or more suture head is disposed in each of two or more delivery needles, with at least one suture bridge interconnecting suture heads disposed in two or more of the delivery needles.

FIGS. 9a to 9k illustrate a tear 804 at least somewhat parallel to the second surface 808. However, tears may form in other locations and orientations and the location of anchoring knots 830 and 846 and the path of the suture between can be altered as appropriate. For instance, a tear (not shown) may form in an orientation essentially orthogonal to the tear 804, in which case the first anchoring knot 830 could be placed on one side of such tear on the second surface 808 the suture being passed through the meniscus to the first surface 806 on the same side of the tear and then being passed along the first surface 806 across the tear and then back through the meniscus on the other side of the tear to the second anchoring knot 846 on the other side of the tear and on the second surface 808. Preferably all knots and other significant protrusions on the suture are kept on the second surface 808 and not on the first surface 806 facing the femur or other surfaces under load such as one which face towards the tibia (not shown).

An embodiment of a single suture head delivery tool 860 that can be used for anchoring suture to tissue at a single location, or for daisy-chaining suture anchoring devices according to the present invention, is schematically illustrated in FIG. 10a in a cross-sectional view 862 and in FIG. 10b in an external view 864. The single head delivery tool 860 resembles the dual head delivery tool 530 disclosed hereinabove.

The single head delivery tool 860 is seen to comprise a cannulated delivery needle 866 having a distal needle end 868, a proximal needle end 870 and a longitudinal needle cannulation 872 therebetween. The delivery needle 866 is proximally coupled to a cannulated handle 874 having a handle wall 876 and a substantially cylindrical handle cannulation 878, the needle cannulation 872 being continuous with the handle cannulation 878. In an embodiment, the needle 866 is proximally reinforced by a stiffening member 880.

A cannulated piston 882 having a distal piston end 884, a proximal piston end 886 and a longitudinal piston cannulation 888 therebetween is seen to be disposed slidably within the needle cannulation 872, and to extend proximally into the handle cannulation 878. The needle 866 can be straight or curved as disclosed hereinabove for the dual head delivery tool 530. A piston positioning member 890 is fixedly connected to the piston 882, and slidably disposed within the handle cannulation 878. In one embodiment, the piston positioning member 890 is an annular member disposed about the piston 882. In an embodiment, the piston positioning member 890 substantially irreversibly locks in position longitudinally when maximally advanced distally within the handle cannulation 878, as disclosed hereinabove for the dual head delivery tool 530.

A control member 892 is connected to the positioning member 890, for positioning the piston 882 longitudinally within the delivery tool 860, from outside the delivery tool 860. The control member 892 can be of the same construction as the control member 564 disclosed hereinabove, or of another construction. The control member 892 extends laterally outward from the positioning member 890, through a slotted opening 894 in the handle wall 876. The slotted opening 894 comprises a longitudinal channel 896 through the handle wall. The longitudinal channel 896 is seen to have a distal channel end 898 and a proximal channel end 900. In one embodiment, as illustrated in FIG. 10, the slotted opening 894 also comprises a transverse channel 902 intersecting the longitudinal channel 896 at an intermediate location between the proximal channel end 898 and the distal channel end 900, providing a "T" shaped opening.

A single head suture anchoring device 904 is seen to be disposed within the single head delivery tool 860, substantially within the needle cannulation 872 and distal to the distal piston end 884. The single head anchoring device 904 comprises a suture head 906 and at least one collapse tail 908 extending proximally from the suture head 906 through the piston cannulation 888. The single head anchoring device 904 can comprise a nonsliding or a sliding suture head. In one daisy-chaining embodiment, the suture head 904 is a nonsliding suture head that also comprises a distal suture loop 910 disposed at the distal end of the suture head 906, and a releasable holding member 912 disposed proximally to the proximal piston end 886, the releasable holding member 912 can be any type of releasable holding member disclosed hereinabove in association with the dual head delivery tool 530.

The releasable holding member 912 prevents the collapse tail 908 from sliding distally through the piston cannulation 888. Further, with the releasable holding member 912 in place, proximally retracting the piston 882 also retracts the suture anchoring device 904, along with the suture loop 910, into the needle cannulation 872 without collapsing the suture head 906 to an anchoring knot. Upon release of the releasable holding member, the collapse tail 908 can slide distally through the piston cannulation 888.

FIG. 11a through FIG. 11i schematically illustrate an embodiment of surgical steps for a daisy-chaining procedure using the single head delivery tool 860 and the daisy-chaining embodiment of the single-head suture anchoring device 904. The daisy-chaining procedure can be performed as part of an arthroscopic procedure or an open surgical procedure wherein a suture tail anchored to tissue is provided by earlier surgical steps. The following description of the procedure references FIG. 10 as well as FIG. 11a through FIG. 11i. Each of FIG. 11a through FIG. 11i includes an illustration of a surgical step, in some of the figures accompanied by an illustration representing a position of the control member 892 in the substantially T-shaped slotted opening 894 as illustrated in FIG. 10.

FIG. 11 *a* illustrates a first step in the daisy-chaining procedure. An anchored suture tail 922 is seen to have been anchored at a first location 924 to tissue 926 having a first surface 928 and a second surface 930. In one embodiment, the anchored suture tail 922 is anchored to the tissue 926 by a first anchoring knot 932 according to the present invention. In another embodiment, the anchored suture tail 922 is anchored to the tissue 926 by another type of suture anchoring device. The anchored suture tail 922 is seen to have been passed through the suture loop 910 of the single head anchoring device 904 disposed in the single head delivery tool 860. The control member 892 is seen to be disposed in the transverse channel 902 of the slotted opening 894.

Figure 11A:
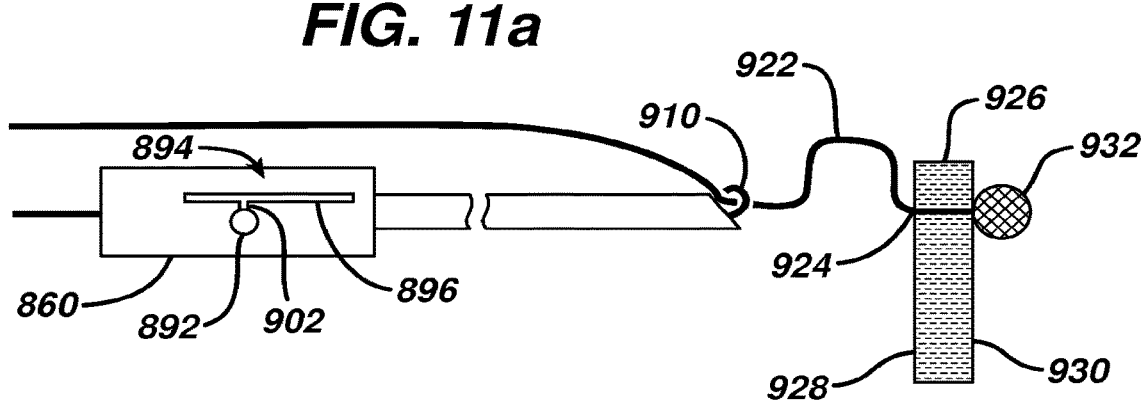
FIG. 11a through FIG. 11i illustrate an embodiment of a daisy-chaining anchoring procedure of the present invention.
Figure 11B:
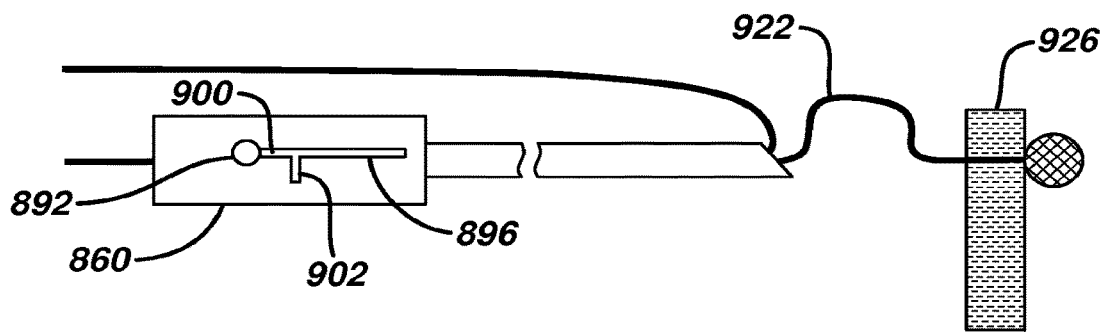
Figure 11C:
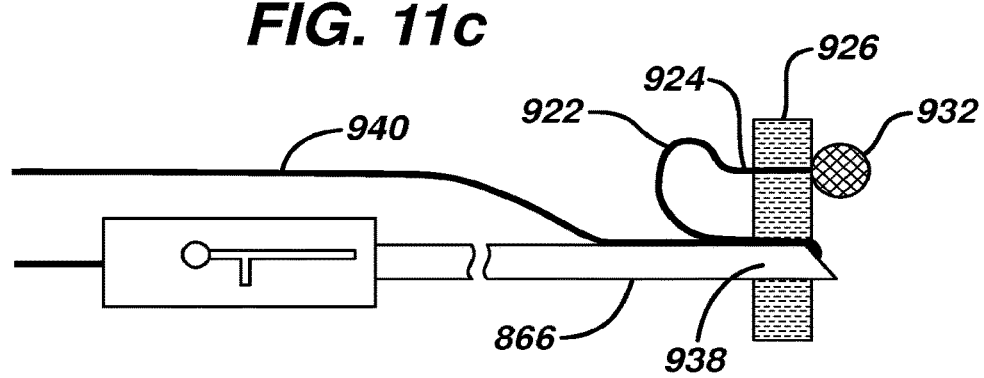

Now referring to FIG. 11*b*, in a second step, the control member 892 is seen to have been moved from the transverse channel 902 to the longitudinal channel 896 and to the proximal channel end 900, retracting the single-head suture anchoring device 904, including the distal suture loop 910, into the distal end of the needle cannulation 872. This retraction step provides retention of the anchored suture tail 922 to the single head delivery tool 860. Now referring to FIG. 11*c*, in a third step, the needle 866 of the single head delivery tool 860, along with the retained, anchored suture tail 922, is seen to have been passed distally through the tissue 926 at a second location 938. The anchored suture tail 922 is seen to bridge the span of the tissue 926 between the first 924 and the second location 938, to pass distally through the tissue 926 alongside the needle 866, through the distal suture loop 910 (inside the needle cannulation 872) and return proximally through the tissue 926 to extend proximally as a tensioning tail 940.

Figure 11D:
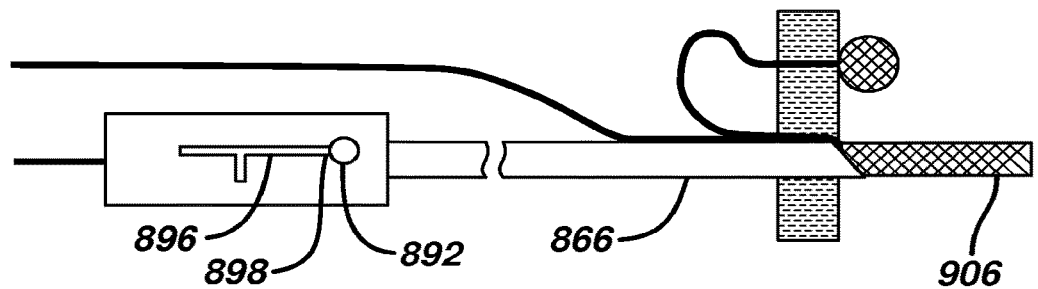
Figure 11E:
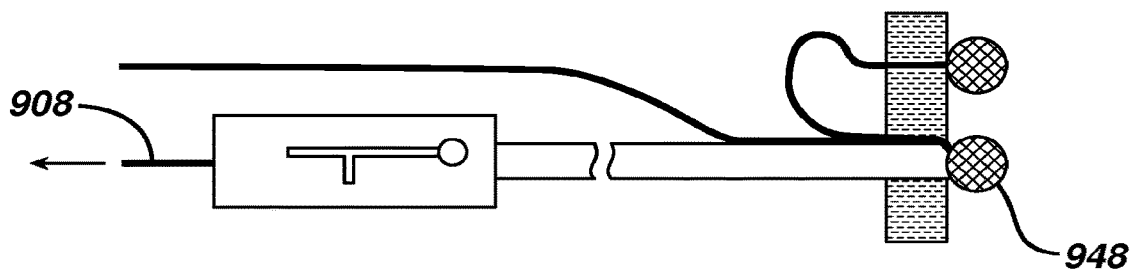
Figure 11F:
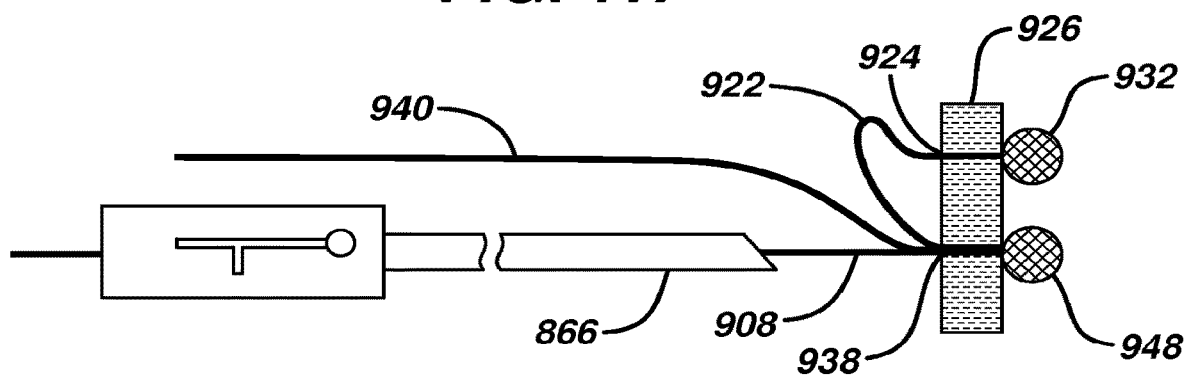

Now referring to FIG. 11*d*, in a fourth step, the control member 892 is seen to have been moved along the longitudinal channel 896 to the distal channel end 898, thereby expelling the suture head 906 distally from the delivery needle 866. Now referring to FIG. 11*e*, in a fifth step, the collapse tail 908 is seen to have been tensioned 946 proximally, thereby collapsing the suture head 906 to a second anchoring knot 948. In addition, the releasable holding member 912 is released in this step. Now referring to FIG. 11*f*, in a sixth step, the delivery needle 866 is seen to have been retracted from the tissue 926, leaving the collapse tail 908 extending from the second anchoring knot 948 and through the piston cannulation 888. The anchored suture tail 922 is seen to bridge the span of the tissue 926 between the first 932 and the second anchor knot 948, passing through the tissue 926 at the first 924 and the second location 938. Further, the tensioning tail 940 extends proximally through the tissue 926 from the second anchoring knot 948.

Figure 11G:
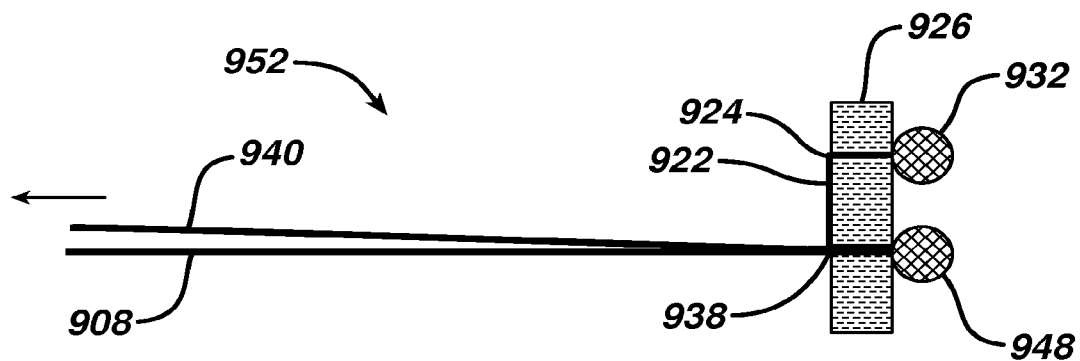

Now referring to FIG. 11*g*, in a seventh step, the single head delivery tool 860 is seen to have been removed entirely from the surgical site, leaving the collapse tail 908 and the tensioning tail 940 extending proximally from the second anchoring knot 948 and through the tissue 926. Proximally tensioning the tensioning tail 940 transmits tension through the distal suture loop 910 (now part of the second anchoring knot 948) to the anchored suture tail 922, thereby shortening the suture between the first 932 and the second anchoring knot 948. In an embodiment, the tissue 926 comprises a tear between the first 924 and the second location 938, and tensioning 954 the tensioning tail 940 applies a closing force to the tear.

Figure 11H:
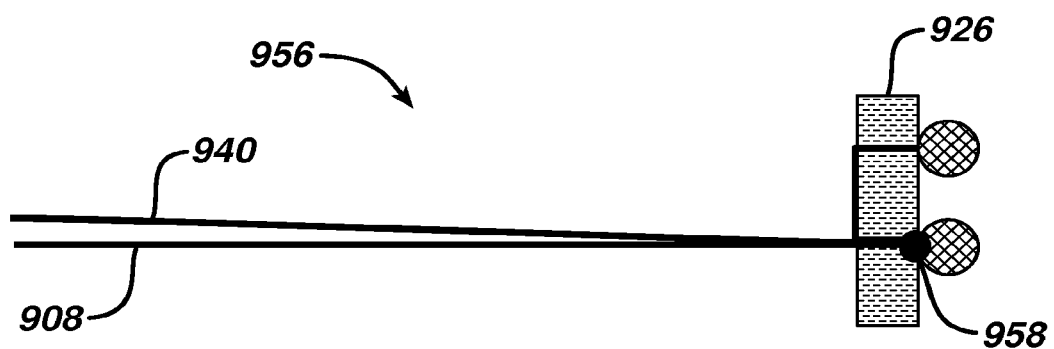
Figure 11I:
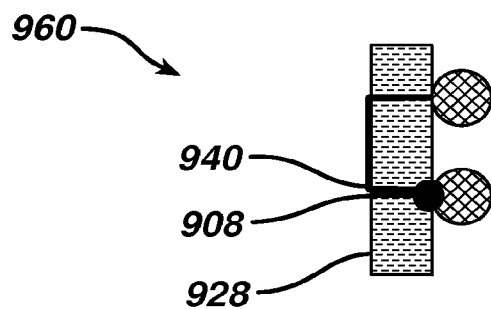

Now referring to FIG. 11*h*, in an eighth step, a knot 958 is seen to have been tied between the tensioning tail 940 and the collapse tail 908 to prevent loosening of the tension applied to the tensioning tail 940 in the seventh step 952. The knot 958 can be positioned adjacent the second anchoring knot 948 using a knot pusher or another known surgical technique. Finally, referring to FIG. 11*i*, in a ninth step, the collapse tail 908 and the tensioning tail 940 are seen to have been trimmed to or below the first tissue surface 928. In an alternate embodiment, one or both of the tensioning tail 940 and the collapse tail 908 is left untrimmed, and is passed through a closed loop of suture extending distally from an additional suture head, to provide a starting point for additional daisy-chaining to other suture anchoring locations.

FIG. 12*a* through FIG. 12*e* schematically illustrate an embodiment of an alternative delivery system and method for anchoring suture to tissue according to the present invention. The alternative delivery system is particularly useful for surgical procedures wherein delivery of a suture head to relatively hard tissue such as cortical bone is required, and for procedures wherein full distal extension of the suture head from a delivery needle is acceptable before collapsing the suture head to an anchoring knot.

Figure 12A:
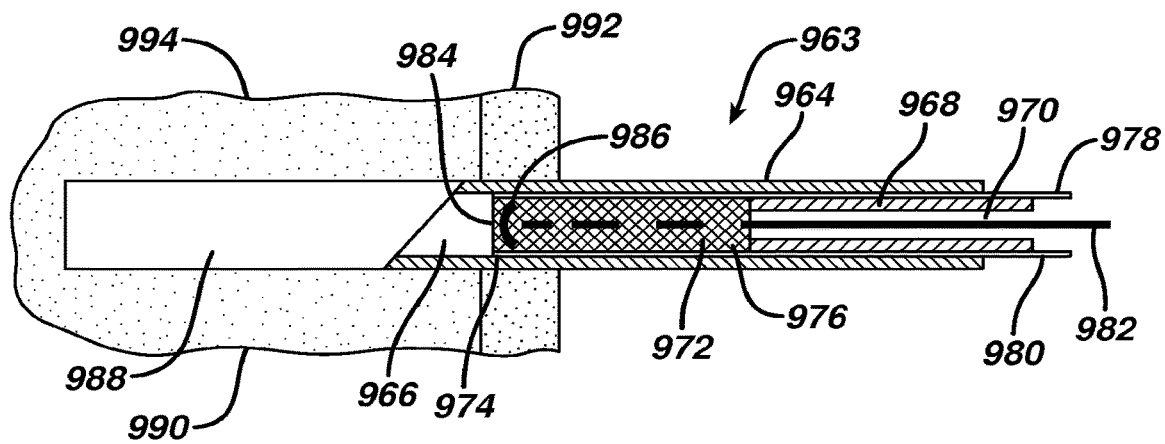
FIG. 12a through FIG. 12e illustrate an embodiment of delivery of suture anchoring devices of the present invention into hard tissue.

Referring to FIG. 12*a*, in a first step, a suture anchoring device 963 is seen to be disposed in a cannulated delivery needle 964 having a longitudinal needle cannulation 966. A longitudinally slidable, cannulated piston 968 having a longitudinal piston cannulation 970 is seen to be positioned within the needle cannulation 966. In an embodiment, the suture anchoring device 963 is a sliding type device comprising a suture head 972 having a distal head end 974, a proximal head end 976 and two collapse tails 978, 980 extending from the proximal head end 976. The collapse tails 978, 980 are seen to be disposed between an exterior surface of the piston 968, and an interior surface of the delivery needle 964. A pusher rod 982 having a distal fork 984 is seen to be disposed through the piston cannulation 970 and distally through or alongside the suture head 972, to engage a portion of suture 986 from which the suture head 972 is configured, in proximity to the distal head end 974. The delivery needle 964 is seen to be positioned in the entrance of an anchoring hole 988 prepared in tissue 990. In the embodiment illustrated in FIG. 12*a* through FIG. 12*e*, the tissue 990 is bone, the anchoring hole 988 penetrating through a cortical layer 992 and into cancellous bone 994. The anchoring hole 988 can be prepared using any surgical drilling or other bone-penetrating method.

Figure 12B:
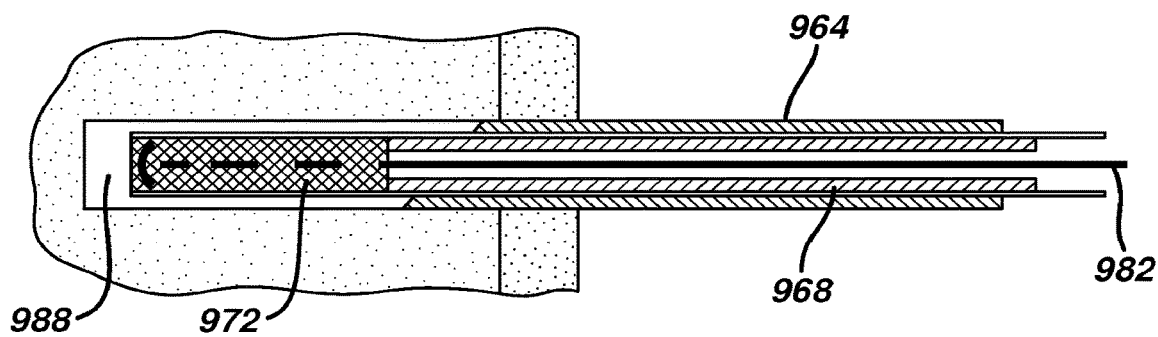
Figure 12C:
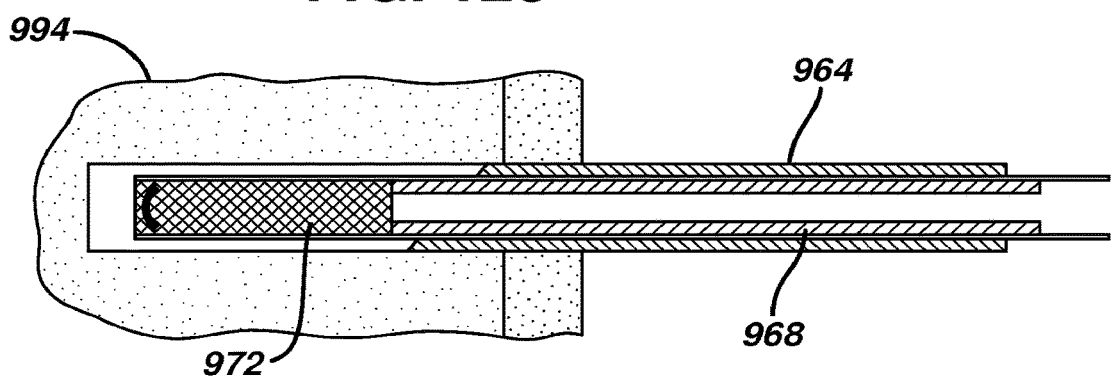
Figure 12D:
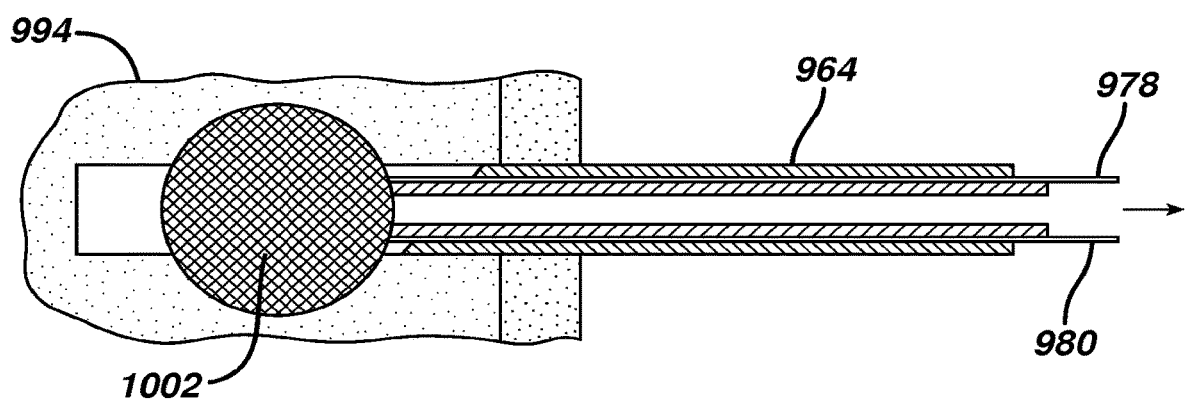
Figure 12E:
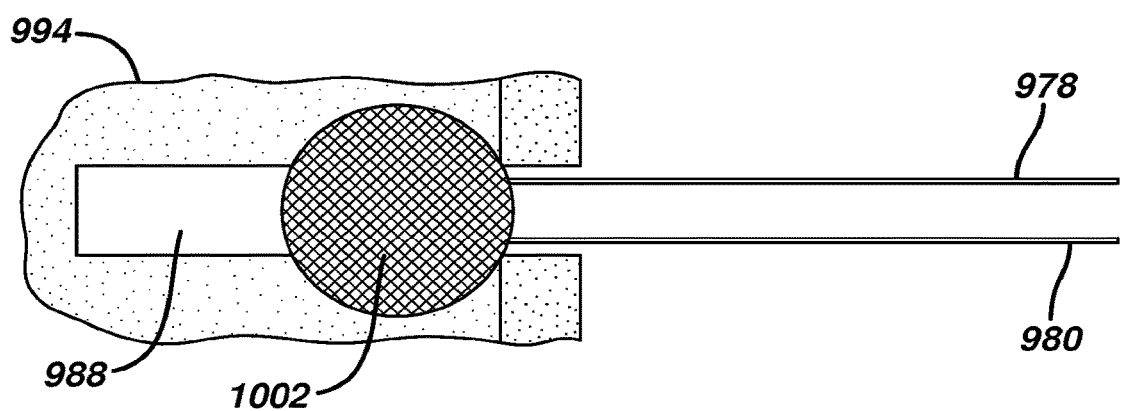

Now referring to FIG. 12*b*, in a second step, the pusher rod 982 is seen to have been used to push the suture head 972 distally from the needle 964 into the anchoring hole 988, with the piston 968 following the distal motion of the suture head 972. In an embodiment, the piston 968 is used in concert with the pusher rod 982 to push the suture head 972 from the needle 964. Now referring to FIG. 12*c*, in a third step, the pusher rod 982 is seen to have been removed, leaving the suture head 972 positioned against the distal end of the piston 968. Now referring to FIG. 12*d*, in a fourth step, the suture head 972 is seen to have been collapsed to an anchoring knot 1002 by proximally tensioning the two collapse tails 978, 980. Now referring to FIG. 12*e*, in a fifth step, the needle 964 and piston 968 therein are seen to have been removed proximally from the anchoring hole 988, leaving the two collapse tails 978, 980 anchored to the tissue 994 and available for further use in a surgical procedure.

Figure 13:
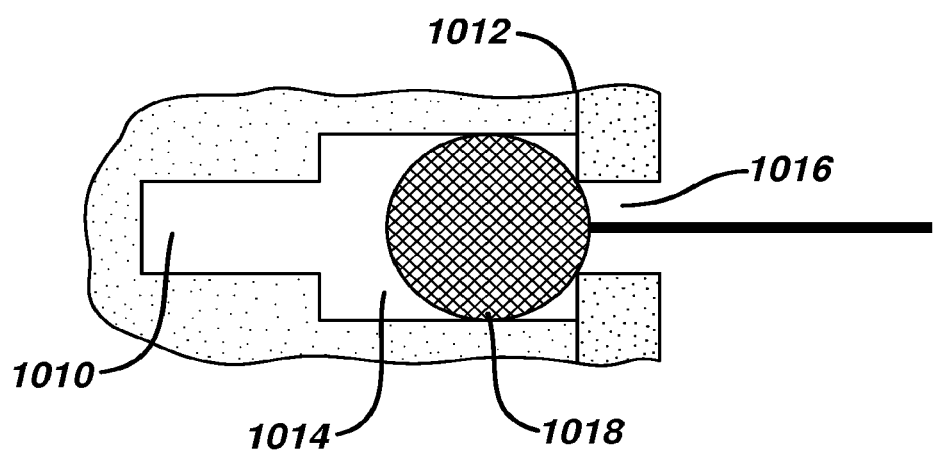
FIG. 13 illustrates an embodiment of a sub-cortically dilated hole in a bone for receiving a suture anchoring device of the present invention.

In particularly hard tissue, such as hard cancellous bone behind overlying cortical bone, tensioning of one or more collapse tail may be insufficient to fully expand a suture head against the walls of a receiving hole in the hard tissue to fully form an anchoring knot. In surgical situations where this may be the case, the diameter of the hole in the cancellous bone is preferably expanded without enlarging the entrance through the cortical bone, before a delivery needle is inserted to deliver the anchoring device. FIG. 13 illustrates a modified anchoring hole 1010 in bone 1012 wherein a cancellous portion 1014 of the anchoring hole 1010 is seen to have been dilated relative to a cortical portion 1016 of the anchoring hole 1010, to accommodate deployment of an anchoring knot 1018. Dilating the cancellous portion 1014 of the anchoring hole 1010 can be accomplished by any means, including but not limited to a curved cutting tool that can be inserted through the cortical portion 1016 of the anchoring hole 1010, a tool that can be inserted into a drilled hole and deployed radially outward from an axis of insertion, a drill bit having a radially deployable cutting member near a distal end, and ultrasonic or other powered cutting tools.

Figure 14A:
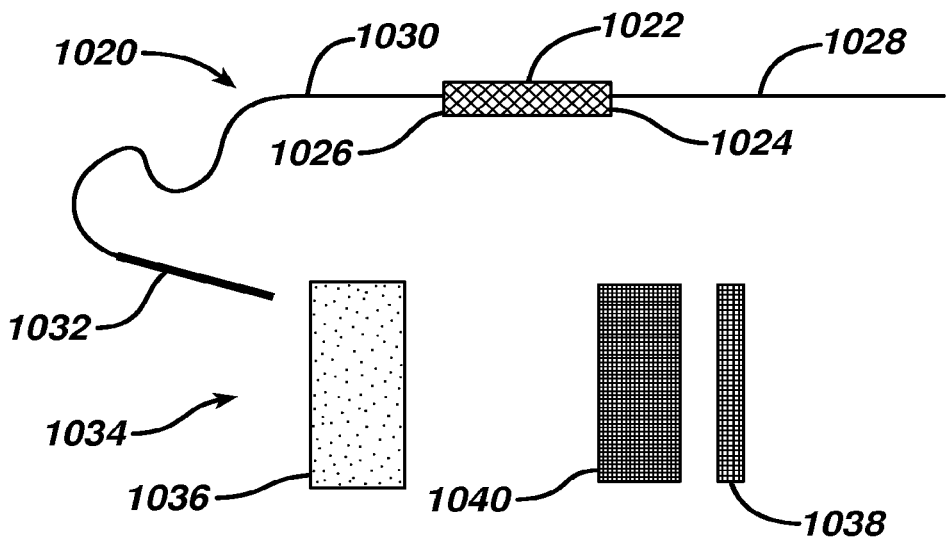
FIG. 14a through FIG. 14d illustrate an alternative embodiment of a delivery device of the present invention.

FIG. 14a through FIG. 14d schematically illustrate an alternative embodiment of a suture anchoring device according to the present invention, and its delivery to tissue, wherein a cannulated delivery needle is not required to deliver a suture head to tissue. Referring to FIG. 14a, a suture anchoring device 1020 is seen to comprise a nonsliding suture head 1022 that can comprise any type of nonsliding suture head disclosed herein. The suture head 1022 is seen to have a first head end 1024 and a second end 1026. Extending from the first end 1024 is a collapse tail 1028, and extending from the second end 1026 is a delivery suture tail 1030 terminated with a tissue-penetrating tool 1032 that in various embodiments is a suturing needle or a surgical guidewire. The delivery tail 1030 is not configured as a collapse tail, so tensioning the delivery tail 1030 with respect to the suture head 1022 does not collapse the suture head 1022 to an anchoring knot.

In an embodiment, the suture anchoring device 1020 is used in a surgical procedure performed from inside 1034 a patient's body, such as an arthroscopic procedure, to anchor suture to a first internal body tissue 1036 underlying the skin 1038 of the patient. In an embodiment, the first internal tissue 1036 also underlies a second internal body tissue 1040 beneath the skin 1038. In one embodiment, the first internal tissue 1036 is a meniscus of a knee, and the second internal tissue 1040 is a joint capsule of the knee.

Figure 14B:
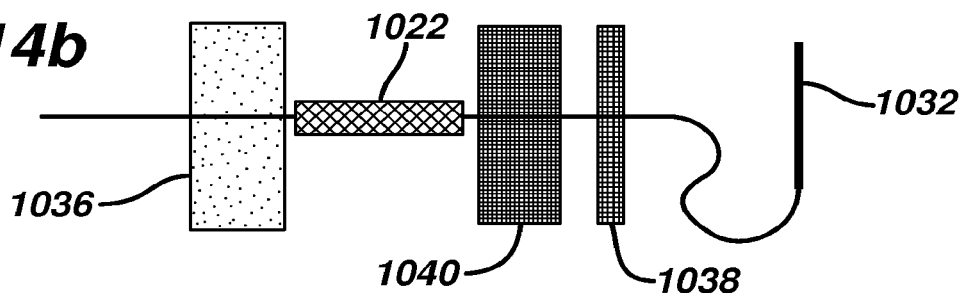
Figure 14C:
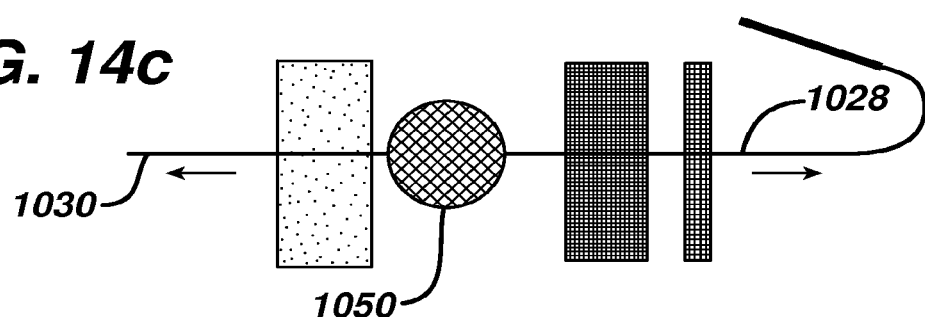
Figure 14D:
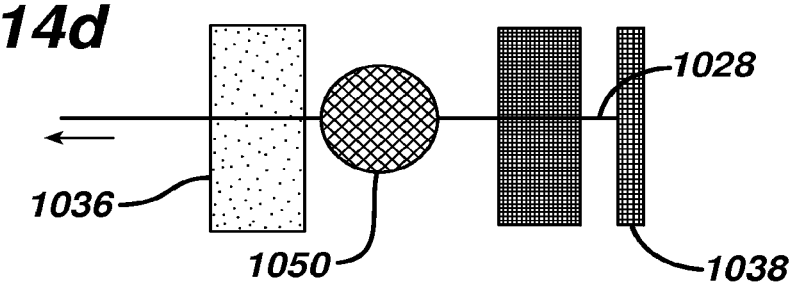

Now referring to FIG. 14b, illustrating a first surgical step, the tissue-penetrating tool 1032 is seen to have been passed from inside 1034 the patient through the first body tissue 1036, the second body tissue 1040 and the skin 1038. In addition, the suture head 1022 has been pulled through the first body tissue 1036, disposing the suture head 1022 between the first body tissue 1036 and the skin 1038. Referring now to FIG. 14c, in a deployment step, the collapse tail 1028 and the delivery tail 1030 are seen to have both been tensioned with respect to the suture head 1022, to collapse the suture head 1022 to an anchoring knot 1050. Finally, now referring to FIG. 14d, in a finishing step, the anchoring knot is seen to have been anchored against the first body tissue by tensioning the collapse tail 1028, and the delivery tail 1030 is seen to have been trimmed, leaving no suture protruding above the skin 1038. The delivery tail 1030, anchored by the anchoring knot 1050, is then available for further use in the surgical procedure, for connection to another tissue or implantable device (not illustrated in FIG. 14a-FIG. 14d).

In addition to providing anchoring of suture directly to tissue, the suture anchoring devices of the present invention disclosed hereinabove can be used to anchor suture to an intermediate implant that itself can be fixed to tissue. The intermediate implant can be any of a variety of implant types including but not limited to a suture anchor, a cannulated screw or rivet, and another implanted object such as a bone plate. Fixation of the intermediate implant to tissue can be by any known means including but not limited to interference, toggling, screw threads, expandable or extendable members, adhesives and cements. FIG. 15a through FIG. 15d illustrate in cross-section, an embodiment of a suture anchoring system and associated method incorporating a suture head that can be any type of suture head disclosed hereinabove, and an intermediate implant for fixation to tissue.

Figures 15A, 15B, 15C, 15D:
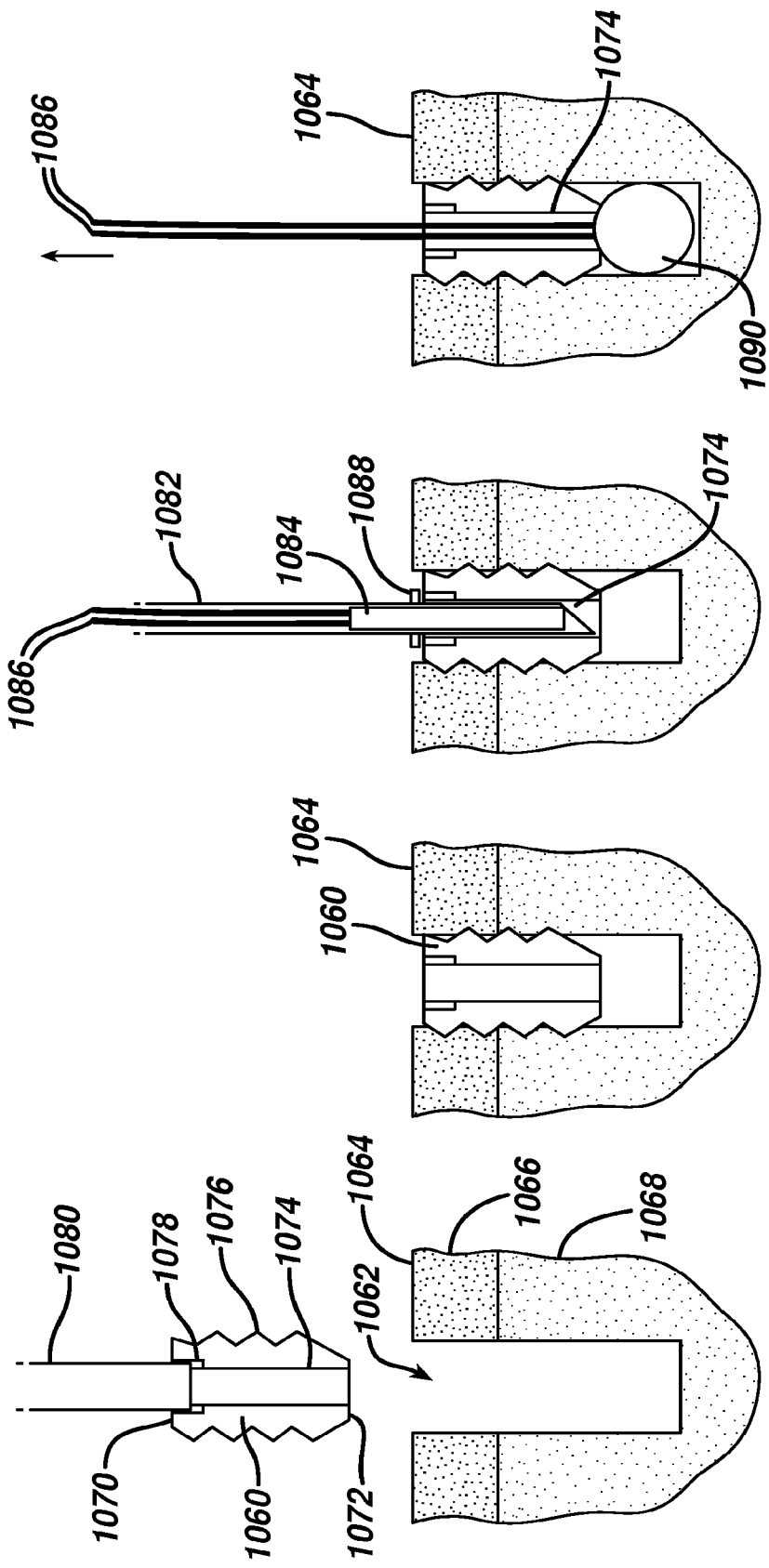
FIG. 15a through FIG. 15d illustrate an embodiment of a suture anchoring system of the present invention wherein a suture head is used in conjunction with an intermediate anchoring implant.

First referring to FIG. 15a, a tissue-anchoring body 1060 is seen to be provided for fixation in a hole 1062 in tissue 1064 that in one embodiment is bone having a cortical layer 1066 and a cancellous layer 1068. The tissue-anchoring body 1060 is seen to have a proximal end 1070, a distal end 1072 and a cannulation 1074 extending therebetween. In an embodiment, the cannulation 1074 has a substantially fixed cross-sectional dimension (diameter, if the cannulation has a circular cross section) along its length. The tissue-anchoring body 1060 is seen to further include one or more external fixation member 1076 for fixing the tissue-anchoring body 1060 in the hole 1062. Any known method can be used for preparing the hole 1062 in the tissue 1064 and for fixing the anchoring body 1060 therein.

In the present embodiment, the one or more fixation member 1076 comprises external screw threads on the anchoring body 1060, for engagement with an inner wall of the hole 1062. The anchoring body 1060 also includes a tool-engaging feature 1078 for releasable connection of a complementary insertion tool 1080 to the anchoring body 1060, for rotationally threading the anchoring body 1060 into the hole 1062. The tool-engaging feature 1078 can comprise a noncircular internal cross-section of the cannulation 1074 along at least a portion of its length between the proximal end 1070 and the distal end 1072. The noncircular cross section can be any type of cross section effective for rotational engagement, such as a hexagonal internal cross-section for receiving the insertion tool 1080, or other configurations including but not limited to square, star-shaped and other screwdriver-type fittings and the like. In another embodiment, the anchoring body 1060 comprises a self-drilling screw that can be fixed into the tissue 1064 without provision of a pre-drilled hole. FIG. 15b illustrates the tissue-anchoring body 1060 fixed to the tissue 1064.

Now referring to FIG. 15c, a delivery tool 1082 for delivering a suture head 1084 comprising one or more proximally extending suture tail 1086, is seen to have been disposed at least partially through the cannulation 1074 from the proximal end 1070 toward the distal end 1072 of the anchoring body 1060. The delivery tool 1082 preferably includes a stop element 1088 that determines a maximum insertion depth of the delivery tool 1082 into the cannulation 1074. With the delivery tool 1082 thus disposed in the cannulation 1074, the suture head 1084 is delivered distally from the delivery tool 1082 using methods and apparatus disclosed hereinabove. Now referring to FIG. 15d, the suture head 1084 is seen to have been delivered distally beyond the distal end 1072 of the cannulation 1074, and collapsed to an anchoring knot 1090 that has a larger cross sectional dimension than that of the cannulation 1074, to resist pullout of the anchoring knot 1090 proximally through the cannulation 1074 when the one or more suture tail 1086 is tensioned. The delivery tool 1082 is also seen in FIG. 15d to have been removed from the cannulation 1074.

In various embodiments, the insertion tool 1080 is removed from the anchoring body 1060 following fixation of the anchoring body 1060 to the tissue 1064, as illustrated in FIG. 15*b*, or left connected to the anchoring body 1060 following fixation. In an embodiment wherein the insertion tool 1080 is left connected to the anchoring body 1060 following fixation of the anchoring body 1060 to the tissue 1064, the insertion tool 1080 is cannulated for receiving the delivery tool 1082 therethrough and to the cannulation 1074. In this embodiment, the insertion tool 1080 also functions as a guide for assisting a surgeon in locating the cannulation 1074 for deploying the suture head 1084.

Another embodiment of a suture anchoring system and associated method incorporating a suture head and an intermediate implant for fixation to tissue is illustrated in FIG. 16*a* through FIG. 16*d*. The embodiment of FIG. 16*a* through FIG. 16*d* resembles the embodiment of FIG. 15*a* through FIG. 15*d*, except that, in the embodiment of FIG. 16*a* through FIG. 16*d*, an anchoring knot is contained substantially within an intermediate implant after deployment, rather than distal to the intermediate implant.

Referring first to FIG. 16*a*, a knot-holding anchoring body 1094 for fixation in the hole 1062 in the tissue 1064 is provided. The knot-holding anchoring body 1094 is seen to have a proximal end 1096, a distal end 1098 and a variable cross-section cannulation 1100 extending therebetween. The knot-holding anchoring body 1094 is seen to resemble the tissue anchoring body 1060 of FIG. 15*a* through FIG. 15*d*, except that the variable cross-section cannulation 1100 is seen to include an enlarged diameter portion 1102 distally spaced from the proximal end 1096. In an embodiment, the variable cross-section cannulation is stepped 1104 in cross-section along its length, having a greater cross-section at the distal end 1098 than at a proximal end 1096. In another embodiment, the variable cross-section cannulation 1094 is substantially closed at the distal end 1098 of the knot-holding anchoring body 1094. FIG. 16*b* illustrates the knot-holding anchoring body 1094 fixed to the tissue 1064.

Now referring to FIG. 16*c*, the suture head 1084 is seen to be disposed in the delivery tool 1084 as described in association with FIG. 15*c*, but, as illustrated in FIG. 16*d*, delivered into the enlarged portion 1102 of the variable cannulation 1100 for collapse to an anchoring knot 1106 disposed substantially within the variable cannulation. In an embodiment, the anchoring knot 1106 conforms to an internal cross section of the enlarged portion 1102 of the variable cannulation 1100. Hybrid embodiments such as those of FIG. 15*a* through FIG. 16*d*, comprising both a suture head and an intermediate implant, are useful, for example, in surgical procedures where a hole or a slot in the intermediate implant is or can be provided for anchoring suture in one or more location on the implant.

Following deployment through a preformed hole or cannulation of a first anchoring device according to the present invention, one or more suture leg extends from a first anchoring knot and proximally through the hole or cannulation. In a multi-anchor embodiment, a cross-sectional dimension of the preformed hole or cannulation is sized to permit passage of a delivery tool for a second anchoring device through the hole or cannulation, alongside the one or more suture leg. Thus sizing the hole or cannulation enables the deployment of two or more anchoring devices through the hole or cannulation, as determined by the surgeon according to the requirements of a surgical procedure.

Suture anchoring devices according to the present invention have many advantages, including but not limited to advantages associated with their structure and materials of construction, versatility of application and delivery, reduced surgical trauma, fixation strength, and failure mode. With regard to materials of construction, suture-anchoring devices according to the present invention advantageously made substantially from suture present no materials compatibility issues between the materials used for an anchor body and suture connected thereto. Further, the present invention can provide suture anchoring devices and associated sutures constructed from a single continuous length of suture, advantageously eliminating all interfaces among anchor components.

In addition, suture-anchoring devices made substantially from suture have no sharp edges or corners that can damage the tissue in which they are implanted. Further, the materials of construction can be selected from among a broad variety of available suture materials, including materials that can provide one or more of great mechanical strength, excellent tissue compatibility, controlled bioabsorbability and tissue ingrowth, and other desirable properties suitable for a surgical repair procedure. Still further, mechanical and chemical treatment of sutures for controlling lubricity, knotting, or chemical elution, is well known in this art and readily applied to entire suture-anchoring devices of the present invention, or to sections thereof by treating only a portion of the suture used to construct a suture anchoring device. Yet further, knotted anchoring configurations themselves provided by the present invention are relatively open structures that can encourage tissue ingrowth for enhanced healing.

Suture anchoring devices according to the present invention are advantageously delivered to tissue via a cannulated delivery needle having a diameter only a few times the diameter of the suture from which the anchoring device is constructed, thereby minimizing surgical trauma associated with the delivery method. Delivery can be to a space behind a tissue wall, or into bulk tissue, for example, into cartilage or into cancellous bone behind a small-diameter penetration through overlying cortical bone. In addition, the cross-sectional size of a deployed anchoring knot in tissue is determined primarily by the length of a suture head disposed in the delivery needle, so a wide range of anchor knot sizes, and therefore deployed retention strengths, can be delivered using a given delivery needle diameter. This feature enables the fixation strength of a repair to be tailored for a specific surgical procedure, up to the failure strength of the suture material, and without such issues as cheese-wiring of anchor materials, or breakage of suture at sharp corners of an anchor body. Also advantageously, if a repair performed using anchoring devices according to the present invention does fail, no potentially injurious sharp-edged or pointed fragments from a failed anchor body are produced.

Suture anchoring devices according to the present invention are particularly advantageous for performing minimally invasive repairs of damaged tissue, such as repairs of soft tissue tears or separations from underlying bone. As one nonlimiting example, a minimally invasive repair of a partial thickness a rotator cuff tear could be performed by passing a small diameter delivery needle containing one or more suture head through tissue of the damaged rotator cuff and into underlying bone of the humerus, for anchoring suture in the bone, for reapproximating the rotator cuff tissue to the bone with minimum surgical trauma.

Because the suture head is flexible, the delivery needle can be shaped to include one or more bend or a curve along its length, for optimizing access to a surgical site and further minimizing surgical trauma. Exemplary shapes of the delivery needle can include a substantially 180 degree U-turn along the needle, as well as any other angle turn, and a helical (corkscrew-shaped) delivery needle. Further, the suture head can be collapsed to an anchoring knot as it is being expelled from the needle, thereby minimizing the penetration depth into or through tissue required for deployment. This feature is particularly advantageous, for example, where anchoring of suture is required to a small bone, or within a shallow space behind a tissue wall. For instance, FIG. 1b shows the suture head 102 protruding in full length beyond the needle 116. However, by simultaneously tensioning the suture tail 112 while forcing the suture head 102 out with the piston 128 rather than the suture head 102 protruding in full length, it just expands into the anchoring knot 136 at the needle distal end 120.

Great breadth of applicability is provided by the present invention, as various embodiments of the suture anchoring devices disclosed herein include either or both of fixed and slidable coupling between an anchoring knot and suture. In addition, a plurality of suture-coupled anchoring devices can be delivered from a single delivery needle. Further, the plurality of anchoring devices in a single delivery needle can include more than one type of anchoring device. Yet further, an adhesive or cement can be injected with the anchoring device, to additionally stabilize a repair.

One skilled in the art will appreciate further features and advantages of the invention based on the above-described embodiments, and that the invention is applicable to open, minimally invasive and robotically-assisted surgery. Further, surgical steps recited herein can be varied in their details, order of execution, and necessity of inclusion in a procedure, without deviating from the intent and scope of the present invention. Accordingly, the invention is not to be limited by what has been particularly shown and described, except as indicated by the appended claims. All publications and references cited herein are expressly incorporated herein by reference in their entirety.

What is claimed is:

1. An anchoring device configured to be anchored in human tissue, the anchoring device comprising:
    a suture length;
    a suture ring defining a circumference,
    wherein a portion of the suture length is wound about the suture ring along at least a majority of the circumference of the suture ring, such that the suture ring and the portion of the suture length collectively define a preformed knot configuration having a first length along a longitudinal direction along an axis of insertion and a first cross-sectional area in a reference plane orthogonal to the axis of insertion; and
    wherein the preformed knot configuration is collapsible into an anchoring knot responsive to tension applied to at least one suture tail of the suture length in a direction away from the preformed knot configuration, the anchoring knot defining a second length along the longitudinal direction and a second cross-sectional area in the reference plane, wherein the second length is shorter than the first length, and the second cross-sectional area is greater than the first cross-sectional area.

2. The anchoring device of claim 1, wherein the at least one suture tail extends away from the suture ring.

3. The anchoring device of claim 2, wherein the at least one suture tail comprises first and second suture tails extending away from the suture ring adjacent one another.

4. The anchoring device of claim 3, wherein the preformed knot configuration is configured to collapse into the anchoring knot responsive to tension applied to the first and second suture tails simultaneously.

5. The anchoring device of claim 4, wherein the preformed knot configuration is configured such that, after collapsing into the anchoring knot, the suture length is slidable through the anchoring knot responsive to tension applied to one of the first and second suture tails.

6. The anchoring device of claim 1, wherein the suture ring is a second suture length.

7. The anchoring device of claim 1, wherein the suture ring comprises a plurality of filaments of suture material interwoven together into a tape-like structure that extends along the circumference.

8. The anchoring device of claim 7, wherein the portion of the suture length is braided together with the tape-like structure along the circumference.

9. A method for anchoring the suture length of claim 1 to a material internal to a human, the method comprising:
    inserting into an opening in a portion of the material the preformed knot configuration along the axis of insertion; and
    tensioning the at least one suture tail in the direction, thereby reconfiguring the preformed knot configuration into the anchoring knot.

10. The method of claim 9, wherein:
    the at least one suture tail comprises first and second suture tails extending away from the suture ring adjacent one another, and
    the tensioning step comprises tensioning the first and second suture tails simultaneously.

11. The method of claim 10, further comprising, after the tensioning step, further tensioning only one of the first and second suture tails, thereby sliding the suture length through the anchoring knot.

12. The method of claim 9, further comprising:
    advancing a delivery tool that carries the preformed knot configuration toward the opening along the axis of insertion during the inserting step; and
    detaching the preformed knot configuration from the delivery tool.

13. An anchoring device configured to be anchored in human tissue, the anchoring device comprising:
    a suture length;
    a suture ring defining a circumference,
    wherein a portion of the suture length is woven through a plurality of penetrations distributed along at least a majority of the circumference, and the portion of the suture length and the suture ring collectively define a preformed knot configuration that defines a first length along a longitudinal direction along an axis of insertion and a first cross-sectional area in a reference plane orthogonal to the axis of insertion,
    wherein the preformed knot configuration is collapsible into an anchoring knot responsive to tension applied to at least one suture tail of the suture length in a direction away from the preformed knot configuration, the anchoring knot defining a second length along the longitudinal direction and a second cross-sectional area in the reference plane, wherein the second length is shorter than the first length, and the second cross-sectional area is greater than the first cross-sectional area.

14. The anchoring device of claim 13, wherein the at least one suture tail comprises first and second suture tails extending away from the suture ring adjacent one another.

15. The anchoring device of claim 14, wherein the preformed knot configuration is configured to collapse responsive to tension applied simultaneously to the first and second suture tails.

16. The anchoring device of claim 15, wherein the preformed knot configuration is configured such that, after collapsing into the anchoring knot, the suture length is slidable through the anchoring knot responsive to tension applied to one of the first and second suture tails.

17. The anchoring device of claim 13, wherein the suture ring comprises a plurality of filaments of suture material interwoven together into a tape-like structure that extends along the circumference.

18. An anchoring device configured to be anchored in human tissue, the anchoring device comprising:
   a suture length;
   a chain of connected suture rings, the chain having a first end and a second end spaced from each other along a longitudinal direction and having a plurality of openings between the first and second ends,
   wherein a portion of the suture length is woven through the plurality of openings such that the portion of the suture length and the chain of connected suture rings collectively define a preformed knot configuration, the preformed knot configuration defining a first length along the longitudinal direction and a first cross-sectional area in a reference plane orthogonal to an axis of insertion oriented along the longitudinal direction,
   wherein the preformed knot configuration is collapsible into an anchoring knot responsive to tension applied to at least one suture tail of the suture length in a direction away from the preformed knot configuration, the anchoring knot defining a second length along the longitudinal direction and a second cross-sectional area in the reference plane, wherein the second length is shorter than the first length, and the second cross-sectional area is greater than the first cross-sectional area.

19. The anchoring device of claim 18, wherein the suture length comprises:
   the portion, wherein the portion is a first portion of the suture length, and the first portion is woven through the plurality of openings along the longitudinal direction;
   a second portion extending alongside the chain of connected suture rings from the second end toward the first end, the second portion extending through a first opening of the plurality of openings at the first end; and
   the at least one suture tail, wherein the at least one suture tail comprises:
      a first suture tail extending from the first portion and away from the preformed knot configuration; and
      a second suture tail extending from the second portion and away from the preformed knot configuration.

20. The anchoring device of claim 19, wherein the preformed knot configuration is configured to collapse responsive to tension applied simultaneously to the first and second suture tails, and the preformed knot configuration is further configured such that, after collapsing into the anchoring knot, the suture length is slidable through the anchoring knot responsive to tension applied to one of the first and second suture tails.

* * * * *